United States Patent
Shapiro et al.

(10) Patent No.: US 6,334,968 B1
(45) Date of Patent: Jan. 1, 2002

(54) METHOD OF FORMING POLYSACCHARIDE SPONGES FOR CELL CULTURE AND TRANSPLANTATION

(75) Inventors: Lilia Shapiro; Rachel Glicklis, both of Beer-Sheva; Smadar Cohen, Petach-Tikva, all of (IL)

(73) Assignee: Ben Gurion University of the Negev, Beer-Sheva (IL)

( * ) Notice: Subject to any disclaimer, the term of this patent is extended or adjusted under 35 U.S.C. 154(b) by 0 days.

(21) Appl. No.: 09/416,911

(22) Filed: Oct. 13, 1999

Related U.S. Application Data

(62) Division of application No. 09/180,970, filed as application No. PCT/IL97/00161 on May 21, 1997.

(30) Foreign Application Priority Data

May 22, 1996 (IL) .................................................. 118376

(51) Int. Cl.[7] .............................................. B29C 71/00
(52) U.S. Cl. .......................... 264/28; 264/41; 264/344
(58) Field of Search ............................ 264/28, 41, 344

(56) References Cited

U.S. PATENT DOCUMENTS

| | | | | |
|---|---|---|---|---|
| 3,653,383 A | * | 4/1972 | Wise | 264/348 |
| 4,393,086 A | * | 7/1983 | Masuyama | 264/109 |
| 4,412,947 A | * | 11/1983 | Cioca | 264/49 |
| 4,522,753 A | * | 6/1985 | Yannas et al. | 264/49 |
| 4,614,794 A | * | 9/1986 | Easton et al. | 530/356 |
| 5,219,361 A | * | 6/1993 | Von Relum et al. | 623/11 |
| 5,366,671 A | * | 11/1994 | Klmura | 264/28 |
| 5,690,996 A | * | 11/1997 | Sanderson et al. | 264/217 |
| 5,700,476 A | * | 12/1997 | Rosenthal et al. | 424/426 |
| 5,888,987 A | * | 3/1999 | Haynes et al. | 514/54 |

FOREIGN PATENT DOCUMENTS

| | | | | |
|---|---|---|---|---|
| EP | 0 648 480 | | 4/1995 | |
| FR | 2167329 | | 1/1972 | |
| JP | 55-71537 | * | 5/1980 | 264/28 |
| JP | 5-125214 | * | 5/1993 | 264/41 |

OTHER PUBLICATIONS

"Biologically Active Analogues of the Exracellular Matrix: Artificial Skin and Nerves", Yannas, Agnew.Chem.Int-.Ed.Engl, pp. 20–335.

"Porous Collagen Sponge for Esophageal Replacement", Natsume, et al. Journal of biomedical Materials Research, vol. 27, pp. 867–875.

Grande et al. J. Orthop.Res, vol. 7, pp. 208–218.

"Selective Cell Translplantation Using Bioabsorbable Artificial Polymers as Matrices", Vacanti, et al. Journal of pediatric Surgery, vol. 23, No. 1, pp. 3–9.

"Prevascularization of porous Biodegradable Polymers", Mikos, et al. Biotechnology and Bioengineering, vol. 42 pp. 716–723.

"Preparation of poly(glycolic acid) bonded fiber structures for cell attachment and transplantation", Mikos, et al. Journal of Biomedical Materials Research, vol. 27 pp. 183–189.

"Laminated three–dimensional biodegradable foams for use in tissue engineering", Mikos, et al. Biomaterials, 1993, vol. 14, No. 5, pp. 323–330.

"Tissue Engineering" Langer, et al. Science vol. 260, May 14, 1993, pp. 920–926.

(List continued on next page.)

Primary Examiner—Allan R. Kuhns
(74) Attorney, Agent, or Firm—Merchant & Gould P.C.

(57) ABSTRACT

A polysaccharide sponge characterized by having: (i) an average pore size in the range between about 10 $\mu$m to about 300 $\mu$m; (ii) an average distance between the pores being the wall thickness of the pores in the range between about 5 $\mu$m to about 270 $\mu$m; and (iii) an E-modulus of elasticity being a measure of the rigidity of the sponge in the range of about 50 kPa to about 500 kPa.

10 Claims, 16 Drawing Sheets

OTHER PUBLICATIONS

"Mechanical stress and cellular metabolism in living soft tissue composites", Jain, et al. Biomaterials, vol. 11, pp. 465–472.

"Fibroblasts Retain Their Tissues Phenotype When Grown in Three–Dimensional Collagen Gels" Doane, et al. Exp..Cell.Res., vol. 195, pp. 432–442.

"Role of cell shape in growth control", Folkman, et al., Nature, vol. 273, Jun. 1, 1978, pp. 345–349.

Madri, et al. Lab.Invest., vol. 66, pp. 139–147.

"Changes in the mechanical properties of dermal sheep collagen during in vitro degradation", Journal of Biomedical Materials Research, vol. 29 pp. 139–147.

"Repair of Articular Cartilage Defects with Collagen–Chondrocyte Allografts", Ben–Yishay, et al. Tissue Engineering, vol. 1, No. 2, pp. 119–132.

"Immunohistology of Collagens, in A Viidik and J. Vuust (Eds.)", Timple, et al., Biol.Collag.Acad.Press, pp. 221.

"Importance of in vitro experimental conditions on protein release kinetics, stability and polymer degradation in protein encapsulated poly(D,L–lactic–acid–co–glycolic acid) microspheres", Park, et al., Journal of Controlled Release, pp. 211–222.

"Acute tissue reactions to potassium alginate with and without colour/flavour additives", Sennerby, et al. Biomaterials, vol. 8, pp. 49–52.

"The pharmacokinetics of, and humoral responses to, antigen delivered by microecncapsulated liposomes" Cohen, et al. Proc.Natl.Sci. USA, vol. 88, pp. 10440–10444.

"Alginate–Polylysine Microcapsules of Controlled Membrane Molecular Weight Cutoff for Mammalian Cell Culture Engineering", King, et al., Biotechnology Progress, vol. 3, No. 4, pp. 231–240.

"Microencapsulated Cells as Hormone Delivery Systems", Sun, et al., CRC Crit.Rev.Drud. Carriers Sys., vol. 4, pp. 1–12.

Matlaga, et al., J. Biomedical Mater.Res. vol. 10, pp. 391–397.

"Use of a Low–Speed, Iso–Density Percoll Centrifugation Method to Increase the Viability of Isolated RAT Hepatocyte Preparations", Kreamer, et al., Biology, vol. 22, pp. 201–207.

Brunk, et al., Analytical Biochem, vol. 92, pp. 497–500.

"ELISA for determination of albumin in the nanogram range: assay in cerebrospinal fluid and comparison with radial immunodiffusion", Schwerer, et al., Clinical Chim., Acta., vol. 163, pp. 237–244.

"Gene Expression During Liver Regeneration", Friedman, et al., J. Mol. Biol, vol. 179, pp. 37–53.

"Fibroblast Seeding and Culture in Biodegradable Porous Substrates", Rivard, et al., vol. 6, pp. 65–68.

"Method for the Quantification of Alginate in Microcapsules", Halle, et al. Cell Transplantation, vol. vol. 2, pp. 429–436.

"High–Yield Preparation of Isolated Rat Liver Parenchymal Cells", Berry, et al., J. Cell.Biol, vol. 43, pp. 506–520.

"Biological Interactions Between Polysaccharides and Divalent Cations: The Egg–Box Model", Grant, et al, FEBS Lett. vol. 32, pp. 195–198.

"Properties of Poly(1,4–hexuronates) in the Gel State", Smidsrod, et al, Acta.Chem.Scand., vol. 26, pp. 79–88.

"Controlled Delivery Systems for Proteins Based on Poly-(Lactic/Glycolic Acid) Microspheres", Cohen, et al., Pharm.Res., vol. 8, pp. 713–720.

"Alginate as Immobilization Material: I. Correlation between Chemical and Physical Properties of Alginate Gel Beads" Martinsen, et al., Biotechnology and Bioengineering, vol. 33, pp. 79–89.

* cited by examiner

US 6,334,968 B1

METHOD OF FORMING POLYSACCHARIDE SPONGES FOR CELL CULTURE AND TRANSPLANTATION

This application is a Divisional of application Ser. No. 09/180,970, filed Nov. 17, 1998, now pending, which is a 371 of PCT/IL97/00161, filed May 21, 1997, which application(s) are incorporated herein by reference.

FIELD OF THE INVENTION

The present invention concerns new bioresorbable polysaccharide sponges, a method for their preparation and uses thereof for the cultivation of mammalian cells in vitro, as well as the use thereof as matrices, supports or scaffolds for implantation into a patient to replace damaged or removed tissue, the polysaccharide sponge implant serving as a substrate, matrix or scaffold for surrounding host tissue to invade it, proliferate thereon and eventually form an active part of the tissue or organ in which the implant was made, or the implant serving as an initial substrate for vascularization from the surrounding host tissue, and once vascularized, cells of choice grown in vitro or obtained from the host may be injected into the vascularized implant to enable a rapid acclimatization and proliferation of the cells which will subsequently form an active replacement for the organ of tissue that was damaged or removed. The polysaccharide sponge can also serve as a substrate, matrix or scaffold for the transplantation of cells initially grown thereon in vitro into a patient to replace damaged, removed or non-functioning tissue.

BACKGROUND OF THE INVENTION AND PRIOR ART

Porous, absorbable matrices fabricated from natural and synthetic polymers (see, for example, Yannas 1990; Natsumi et al., 1993; Grande, 1989; Vacanti, 1990; Mikos et al., 1993a; Mikos et al., 1993b Mikos et al. 1993c; and Langer and Vacanti, 1993), currently in use or under investigation as implants to facilitate regeneration of tissue in defects caused by disease, trauma or reconstructive surgical procedures. These matrices have been used alone or seeded with cells for the purpose of cell and tissue transplantation (Langer and Vacanti, 1993). Cell transplantation can provide an alternative treatment to whole organ transplantation for failing or malfunctioning organs such as liver and pancreas. As many isolated cell populations can be expanded in vitro using cell culture techniques, only a very small number of donor cells are needed to prepare a suitable implant. Consequently, when such cells are taken from a living donor, the living donor need not sacrifice an entire organ. Furthermore, for the purpose of gene therapy, gene transfer vectors can be introduced into various types of cells, such as, for example, hepatocytes, fibroblasts, keratinocytes, endothelial cells, and myoblasts, which are then transplanted back to the host for the production and local release of proteins and other therapeutic drugs or agents.

Another application of porous matrices has been as scaffolds to investigate the behavior of cells in a three-dimensional framework in vitro (Jain et al., 1990; Doane and Birk, 1991). In some applications, these porous matrices are designed to serve as analogues of the extracellular matrix in order to provide a suitable substrate for cell attachment to enable certain anchor-dependent processes such as migration, mitosis, and matrix synthesis (Folkman and Moscona, 1978). In this regard, it is considered that such analogues of the extracellular matrix may be able to modulate cell behavior in a similar fashion to the way in which the native extracellular matrix does so (see Madri and Basson, 1992), it being believed that the chemistry of these analogues, as well as their pore characteristics such as percentage porosity, pore size and orientation, may influence the density and distribution of the cells within the matrix and thereby affect the regeneration process when these analogues are used in transplantations.

Bioresorbable sponges can also provide a temporary scaffolding for transplanted cells, and thereby allow the cells to secrete extracellular matrix of their own to enable, in the long term, a complete and natural tissue replacement. The macromolecular structure of these sponges is selected so that they are completely degradable and are eliminated, once they have achieved their function of providing the initial artificial support for the newly transplanted cells. For these sponges to be useful in cell transplantations, they must be highly porous with large surface/volume ratios to accommodate a large number of cells, they must be biocompatible, i.e., non-toxic to the cells that they carry and to the host tissue into which they are transplanted, they must be capable of promoting cell adhesion and allowing the retention of the differentiated function of attached cells.

However, in most of the porous matrices described to date, the ones that have been successfully prepared and used in implants or transplants have been limited to those which carry a very thin layer of cells, being principally those which serve as skin substitutes or replacements (see, for example, Yannas, 1990). In view of this limited application, the matrices developed are ones in which the porosity and pore size thereof has been of the type that has been nearly sufficient to allow the dispersion of the thin layer of cells within the matrix. However, when such matrices are to be used with cells such as, for example, hepatocytes, which grow in aggregates of cells and with a thickness greater than the thickness which these earlier matrices are designed to support, a serious problem arises as regards the adequate diffusion of oxygen and nutrients to the inner cells within the matrix, with the result that these inner or lower layers of cells usually die. Thus, these earlier matrices may be useful for preparing skin equivalents, but are much less useful for preparing functional organ equivalents made up of multi-layer cell aggregates, both in vitro and with subsequent transplantation use in vivo.

Most of the porous matrices developed to date, as noted above, are based on natural polymers such as collagen, or synthetic polymers from the lactic/glycolic acid family. The collagen-based matrices have several disadvantages, including: they degrade at relatively rapid rate; many disappearing as early as 4 weeks postimplantation (see Olde Damink et al., 1995; Ben-Yishay et al., 1995). Although the rate of degradation of the collagen matrix may be reduced by cross-linking with glutaraldehyde, the resulting cross-linked matrices, however, exhibited immunogenicity, calcification, and fibrous scarring when implanted for long periods (see Timple et al., 1980). Furthermore, collagen matrices are also not suitable for prolonged in vitro cultivation of cells due to a significant contraction of the collagen scaffold, which occurs after approximately one week of incubation, rendering this collagen scaffold less amenable to surgical handling when intended for use as a transplantation matrix (Ben-Yishay, 1995).

Other synthetic biodegradable foams based on poly(D, L-Lactic-co-glycolic acid) have been developed as scaffolds for tissue engineering, as noted above, but because these polymers are hydrophobic, when a cell suspension or culture media is placed on these foams or injected into their interior, the majority of their pores remain empty, resulting in he underutilization of the volume of these foams. In addition, studies have also shown that the degradation of these biodegradable foams results in the signifcant accumulation of acid products which significantly decreases the internal pH within the foam to less than pH 3.0 (see Park Lu and Crotts, 1995), which acidity is very harmful to the growing cells.

Alginates have also been used previously for the purpose of cell transplantation. Aiginates are natural polysaccharide polymers, the word "alginate" actually referring to a family of polyanionic polysaccharide copolymers derived from brown sea algae and comprising 1,4-Linked β-D-mannuronic (M) and α-L-gluronic acid (G) residues in varying proportions. Alginate is soluble in aqueous solutions, at room temperature, and is capable of forming stable gels, particularly in the presence of certain divalent cations such as calcium, barium, and strontium. The unique properties of alginate, together with its biocompatibilty (see Sennerby et al., 1987 and Cohen et al., 1991), its relatively low cost and wide availability have made alginate an important polymer in medicinal and pharmaceutical applications. For example, it has been used in wound dressings and dental impression materials. Further, alginate has also been approved by various regulatory authorities as acceptable for use as a wound dressing and as food additives in humans. Moreover, pharmaceutical grade alginates, which comply with all the quality and safety requirements of the European and United States of America (USA) pharmacological regulatory authorities, are readily available from several commercial manufacturers. Thus, while alginate has been used for cell transplantation, these previous efforts have generally focused on systems in which a semipermeable membrane was developed as deemed necessary for the protection of cells from the host immune system (see, for example, King et al., 1987 and Sun et al., 1987). These semipermeable membranes were prepared by dropping a mixture of the cells suspended within an alginate solution into a second solution contain calcium chloride. This yielded alginate beads or microcapsules which encapsulated the cells carried thereby. Microcapsules are usually also subjected to a second step in which a semipermeable membrane is formed around the alginate bead by the adsorption of a polycation, such as polylysine, onto the surface of the beads. This coating, however, greatly reduces the microcapsule permeability towards nutrients, which leads to the death of the encapsulated cell.

In view of the above drawbacks of the prior art, it is the aim of the present invention to provide a polysaccharide polymer scaffold made from any suitable polysaccharide polymer, such as, for example, alginates, gellan, gellan gum, xanthan chitosan, agar, carrageenan (polyanionic polysaccharide polymers), or chitosan (polycationic polysaccharide polymers), which provides adequate sites for the attachment and growth of a sufficient cell mass to survive and function not only in vitro but also in vivo, and which polysaccharide polymer scaffold, substrate or matrix, also does not limit the survival and growth of only those cells adjacent to the matrix surface as the cells increase in number within the matrix, but rather also serves to support thick layers of cells, such as cell aggregates, and is capable of maintaining the cells in an active functional state before and after implantation/transplantation into a host tissue, at which time this polysaccharide matrix will also be amenable to vascularization from the surrounding tissue (antgienesis).

It is another aim of the invention to provide polysaccharide matrices which are biodegradable but which de grade only slowly in vivo and thereby permit the cells carried thereby to become established and to form their own tissue matrix at the site of transplant to the point where they no longer require the polysaccharide matrix; or when the matrix is used alone as an implant, it is to be stable for sufficient time for the surrounding tissue to invade it and proliferate thereon to the point where the invasive cells have become established and have formed their own tissue matrix, thereby replacing the originally deficient tissue; or when the matrix is used alone as a first stage of an implant, it is to be stable for sufficient time to allow for vascularization from the surrounding tissue into the implant to occur by invasion thereof by blood vessels, and to allow for the second stage in which cells of choice can be injected into the vascularized matrix and subsequently proliferate thereon to the point where these cells have become established, have formed their own tissue matrix, and thereby have replaced, at least functionally, the originally deficient or damaged tissue.

Yet another aim of the present invention is to provide such polysaccharide sponges of a highly porous nature that may be readily invaded by blood vessels and/or cells and subsequently which may adequately support the growth, proliferation and biological function of such implanted or transplanted cells, both in vitro and afterwards in vivo when used in implants or transplants, such polysaccharide sponges being of a morphology such that their internal volume is optimally utilized, and further providing such sponges which do not require any form of external coating or the like for the purposes of implantation or transplantation, and hence the sponges will not be simply vehicles for the encapsulation of cells but rather would serve as a matrix or scaffold for the cells which they carry and permit free transport of oxygen and nutrients into the cells and in vivo provide for vascularization of the cells for the purposes of nutrient supply and subsequent tissue regeneration from these transplanted cells. Hence, the polysaccharide sponges of the present invention are designed not to serve as merely encapsulation devices for cells but rather as effective matrices, supports or scaffolds for optimal use in implantations and transplantations for tissue repair, as noted above.

A still further object of the present invention is to provide a method for the production of the polysaccharide sponges of the invention.

Other aims of the invention include providing polysaccharide sponges for use in vitro mammalian cell culture, in implantations and in transplantations for repair of damaged or diseased tissue, as well as the use of such polysaccharide sponges for these purposes of in vitro cell culture, implantations and transplantations.

Other objects and aspects of the invention will be readily apparent from the following description of the invention or will arise clearly therefrom.

SUMMARY OF THE INVENTION

The present invention is based on a new method for the preparation of three-dimensional, porous, biodegradable sponges and the sponges produced thereby, which sponges are made from any suitable polysaccharide such as, for example, polyanionic polysaccharide polymers, which include alginates, gellan, gellan gum, xanthan chitosan, agar, carrageenan, and polycationic polysaccharide polymers which include chitosan. The polysaccharide sponges of the invention have many possible applications, in particular, medical applications such as, for example, they may be used as a cell matrix, substrate or scaffold to grow various mammalian cells in vitro under conditions that will provide for the obtention of such mammalian cells in vitro that are in an active stage of cell proliferation or even at stages of differentiation with related biological activity of the cells at these stages. Such cellular growth, activation and/or differentiation and/or proliferation is fully dependent on the nature of the substrate, matrix or scaffold on or in which they are grown, and in this regard the new alginate sponges of the invention have been shown to be particularly advantageous for the growth of mammalian cells such as, for example, fibroblasts and hepatocytes. Moreover, mammalian cells grown on or within the polysaccharide sponges in accordance with the present invention may be used in auto and allo transplants for the purposes of, for example, replacing damaged organs or tissues, such as for example skin, liver and many others. Likewise, the polysaccharide sponges of the invention also are particularly useful as implants being inserted into a patient to replace tissue that has been damaged, or removed and which implants are intended to fill the space left by the damaged or removed tissue and to allow for the surrounding tissue to invade the implant and ultimately to fill the implant with the cellular material to restore the originally damaged or removed tissue. Such implants may also be used in a two-stage procedure, in which, in the first stage the implant is inserted into a patient to replace tissue or an organ that has been completely or partially removed. The implant is then invaded by blood vessels from the surrounding tissue, to provide vascularization of the implant, this taking place shortly after implantation. Once the implant has been vascularized, the second stage is performed by injecting into the implant cells of choice which are intended to replace the original tissue/organ. These cells have been previously cultured in vitro or have been obtained fresh from the patient or a suitable donor. Once injected the cells are capable of a rapid acclimatization due to the preformed vascular network in the implant from the first stage. As a result, the injected cells can rapidly proliferate and fill the implant and subsequently differentiate to various stages and ultimately provide an active replacement for the originally damaged or removed tissue/organ. The nature of the polysaccharide sponges of the invention are particularly useful for the aforesaid transplantation or implantation applications in that the polysaccharides of choice are those having a very low immunogenicity, a stability for relatively long periods of time, and because the sponges are biodegradable they will eventually, after a relatively long period of time, be broken down within the body without any deleterious side effects.

The porosity and sponge morphology of the polysaccharide sponges of the invention are dependent on various formulation and processing parameters which may be varied in She process of the invention, and hence it is possible to produce a wide variety of sponges of macroporous nature suitable for cell culture and vascularization. The various sponges have good mechanical properties and hence are suitable, as noted above, to support the growth and proliferation of a wide variety of mammalian cells, such as, for example, fibroblasts and hepatocytes, and thereby the sponges of the invention seeded with such cells can provide at least a temporary support for such cells when transplanted to replace, for example, skin (dermis fibroblasts) or liver (hepatocytes) tissue. This temporary support will be for the period until which the cell transplanted sponge is biodegraded with the patient, at which time it would be expected that by way of the transplant, the originally damaged or diseased tissue would have been able to repair itself.

The new process of the invention is based on a three-step procedure involving a gelation step in which a polysaccharide solution is gelated in the presence of a cross-linking agent, followed by a freezing step, and finally a drying step, by lyophilization, to yield a porous sponge. By altering the conditions at each stage, in particular the concentration of the polysaccharide, the presence or absence of a cross-linking agent and the concentration thereof, the shape of the vessel in which the gelation step is carried out, and the rapidity of the freezing step, it is thereby possible to obtain a very broad range of polysaccharide sponges of various shapes, having various pore sizes and distribution and hence also varying mechanical properties.

The following meanings of various terms will be used herein throughout:

Pore size—The pore size of a pore within a polysaccharide sponge is determined by using the equation $$d = \sqrt{l \times h},$$

wherein l and h are the average length and width of the pores, respectively, as determined by microscopic analysis of the various sponges (see Example 2).

Pore wall thickness—This parameter characterizes the distance between the pores within a sponge and hence is indicative of the microstructure of the sponges and is determined also by measurement at the microscopic level of the various sponges (see Example 2).

E-modulus of elasticity—This is a measure of the relative rigidity of the polysaccharide sponges and is determined in units of kPa when subjecting sponges to compression and monitoring the rate of their deformation. The higher the E-modulus of elasticity, the higher is the relative rigidity of the sponge.

Polysaccharide solutions—This is taken to mean two kinds of solutions, the first being the original solution of the polysaccharide in water, prepared by dissolving under conditions of homogenization, a commercially available form of the polysaccharide in water, usually yielding a solution of the salt of the polysaccharide, for example, a sodium alginate solution. This initial solution is then subjected to gelation as the first step in the sponge preparation process of the invention. The solution subjected to gelation is called the final polysaccharide solution, and in many cases is a further diluted form of the initial polysaccharide solution. Hence, when concentrations of polysaccharide are indicated herein throughout, they usually refer to the concentration of the polysaccharide in the final solution that was subjected to the gelation step in the first part of the process from which the polysaccharide sponge is obtained. In the examples herein below there is exemplified a variety of sponges made from but one of the polysaccharides of choice, namely, various alginates. Hence, in accordance with the above-mentioned, there will be used "original alginate solution" or "initial alginate solution" to indicate the aqueous alginate solution fast form by dissolving an alginate powder in water, and "final alginate solution" to indicate the dissolved alginate solution subjected to gelation and subsequent freezing and drying.

Implantation—This term is usually meant to imply the insertion of a polysaccharide sponge of the invention into a patient, whereby the implant serves to replace, fully or partially, tissue that has been damaged or removed with the implant serving, as a matrix, substrate or scaffold on which surrounding tissue which may invade the implant and may grow so that ultimately, following sufficient growth of such tissue within the sponge and with the biodegradation of the sponge over time, the injured or removed tissue will be effectively replaced. Implantation in this sense also means the above-noted two-stage procedure in which, in the first stage, the implant is placed into the patient and becomes vascularized by invasion of blood vessels from surrounding tissue, a process which usually occurs rapidly following implantation. Once vascularized, the implant is then accessible to the second stage being the the injection thereinto of cells of choice either grown previously in vitro or obtained from the patient or a suitable donor. Such cells are capable of a rapid acclimatization because of the pre-formed vascular network within the implant, and hence are also capable of a rapid proliferation and subsequent functional differentiation to provide a replacement for the damaged or removed tissue. In fact, when it is necessary to fully replace a tissue/organ, for example, skin or liver segments or portions that have been removed, then there is a need to apply the above two-stage procedure. In this way functional cells, for example, fibroblasts or hepatocytes, will be infected into the implant which has already been vascularized. Another aspect of implantation is also take to mean the use of a polysaccharide sponge as a vehicle to transport therapeutic drugs to a certain site in a patient, usually by, way of cells carried by the polysaccharide sponge which are capable of secreting a desired therapeutic protein, hormone or the like, or which secrete various regulatory proteins which in turn can direct the expression of such required therapeutic drugs endogenously within the tissue in which the implant has been inserted. In this aspect there is also included the introduction into the polysaccharide sponge of encapsulated therapeutic agents, for example, growth factors, angiogenic factors, and the like, which are advantageous to encourage a more rapid growth of the cells within the implant, or a more rapid vascularization of the implant. Such factors are usually too small to be effectively retained within the sponge and hence are introduced in the form of slow-release or controlled-release microcapsules into the sponge to provide for their effectivity.

Transplantation—Transplantation may be of two kinds, i.e., allo or auto transplantation, and in both cases, the cells to be transplanted will first be grown, in vitro on or within the alginate sponge until they reach a desired state of cell activation, proliferation of differentiation as required, at which time the alginate sponge with such seeded cells will be transplanted into a patient at the desired site for the purposes of organ or tissue repair, or replacement. As noted above, the transplantation can also include, besides the cells, microcapsules containing therapeutic agents for the cells, vascularization or for the host.

Accordingly, the present invention provides a polysaccharide sponge characterized by having: (i) an average pore size in the range between about 10 $\mu$m to about 300 $\mu$m; (ii) an average distance between the pores being the wall thickness of the pores in the range between about 5 $\mu$m to about 270 $\mu$m and (iii) an E-modulus of elasticity being a measure of the rigidity of the sponge in the range of about 50 kPa to about 500 kPa.

An embodiment of the sponge of the invention is a sponge which comprises a polysaccharide selected from the group comprising the polyanionic polysaccharides: alginates, gellan, gellan gum, xanthan chitosan, agar, carrageenan and the polycationic polysaccharide: chitosan.

Another embodiment of the polysaccharide sponge of the invention is a sponge which comprises an alginate selected from the group of alginates characterised by having: (i) a mannuaronic acid (M) residue content in the range of between about 25% and about 65% of total residues: (ii) a guluronic acid (G) residue content in the range of between about 35% and about 75% of total residues; (iii) a M/G ratio of about 1/3 and about 1.86/1; and (iv) a viscosity of the final alginate solution having 1% w/v alginate, from which the sponge is obtained in the range between about 50 cP to about 800 cP.

Preferred polysaccharide sponges of the invention include sponges comprising an alginate derived from brown sea algae selected from the group consisting of alginate Protanal™ LF 120 (LF 120) derived from *Laminaria hyperborea*, alginate Protanal™ LF 20/60 (LF 20/60) derived from *Laminaria hyperborea*, alginate MVG™ (MVG) derived from *Laminaria hyperborea*, alginate Pronatal™ HF 120 (HF 120) derived from *Laminaria hyperborea*, alginate Pronatal™ SF 120 (SF 120) derived from *Laminaria hyperborea*, alginate Pronatal™ SF 120 RB (SF 120 RB) derived from; *Laminaria hyperborea*, alginate Pronatal™ LF 200 RB (LF 200 RB) derived from *Laminaria hyperborea*, alginate Manugel™ DMB (DMB) derived from *Laminaria hyperborea*, Keltone™ HVCR (HVCR) derived from *Macrocystis pyrifera*, and Keltone™ LV (LV) derived from *Macrocystis pyrifera*.

The above alginate sponges of the invention preferably are formulated wherein the alginate is used in the form of a sodium alginate solution having a concentration of alginate between about 1% to about 3% w/v to provide an alginate concentration between about 0.1% to about 2% w/v in the final solution from which the sponge is obtained.

In accordance with yet another embodiment of the invention, the polysaccharide sponges may also comprise a cross-linking agent selected from the group consisting of the salts of calcium, copper. aluminum, magnesium, strontium, barium, tin, zinc, chromium, organic cations, poly(amino acids), poly(ethyleneimine), poly(vinylamine), poly(allylamine), and polysaccharides.

The most preferred cross-linking agents for use in the preparation of the sponges of the invention are selected from the group consisting of calcium chloride ($CaCl_2$), strontium chloride ($SrCl_2$) and calcium gluconate (Ca-Gl).

Preferably, the cross-linker is used in the form of a cross-linker solution having a concentration of cross-linker sufficient to provide a cross-linker concentration between about 0.1% to about 0.3% w/v in the final solution from which the sponge is obtained.

The preferred polysaccharide sponges of the invention are those which are prepared from a polysaccharide solution with or without the addition of a cross-linker. Embodiments of these preferred sponges of the invention include an alginate sponge prepared from an alginate solution with or without the addition of a cross-linker and wherein said final alginate solution with or without cross-linker from which said sponge is obtained is selected from the group of final solutions, having concentrations of alginate or alginate and cross-linker, consisting of: (i) LF 120 alginate 1% w/v without cross-linker; (ii) LF 120 alginate 1% w/v and Ca-Gl 0.1% w/v; (iii) LF 120 alginate 1% w/v and Ca-Gl 0.2% w/v; (iv) LF 120 alginate 1% w/v and $SrCl_2$ 0.15% w/v; (v) LF 120 alginate 1% w/v and $CaCl_2$ 0.1% w/v; (vi) LF 120 alginate 0.5% w/v and Ca-Gl 0.2% w/v; (vii) LF 20/60 alginate 1% w/v and Ca-Gl 0.2% w/v; (viii) HVCR alginate 0.5% w/v and Ca-Gl 0.2% w/v; and (ix) HVCR alginate 1% w/v and Ca-Gl 0.2% w/v.

Other such embodiments include sponges obtained from a final solution of LF 120 alginate 1% w/v and Ca-Gl cross-linker 0.2% w/v; and a sponge obtained from a final solution of HVCR alginate 1% w/v and Ca-Gl cross-linker 0.2% w/v.

The present invention also provides a process for producing a polysaccharide sponge of the invention comprising:

(a) providing a polysaccharide solution containing about 1% to about 3% w/v polysaccharide in water;

(b) diluting said polysaccharide solution with additional water when desired to obtain a final solution having about 0.5% to about 2% w/v polysaccharide, and subjecting said solution of (a) to gelation, to obtain a polysaccharide gel;

(c) freezing the gel of (b); and (d) drying the frozen gel of (c) to obtain a polysaccharide sponge.

An embodiment of the above process of the invention is a process further comprising the addition of a cross-linker to said polysaccharide solution of (a) during the step of elation (b), said cross-linker being added in an amount to provide a concentration of cross-linker in the final solution being subjected to gelation of between about 0.1% to about 0.3% w/v.

In a preferred embodiment of the gelation step (b) of the process of the invention, the gelation is carried out by intensive stirring of the polysaccharide solution in a homogenizer at about 31800 RPM for about 3 minutes, and wherein when a cross-linker is added to the solution, said cross-linker is added very slowly during said intensive stirring of the alginate solution.

In a preferred embodiment of the process of the invention, there is provided a process wherein the polysaccharide is an alginate selected from the group consisting of an alginate derived from brown sea algae selected from the group consisting of alginate Protanal™ LF 120 (LF 120) derived from *Laminaria hyperborea*, alginate Protanal™ LF 20/60 (LF 20/60) derived from *Laminaria hyperborea* alginate MVG™ (MVG) derived from *Laminaria hyperborea*, alginate Pronatal™ HF 120 (HF 120) derived from *Laminaria hyperborea*, alginate Pronatal™ SF 120 (SF 120 ) derived from *Laminaria hyperborea*, alginate Pronatal™ SF 120 RB (SF 120 RB) derived from *Laminaria hyperborea*, alginate Pronatal™ LF 200 RB (LF 200 RB) derived from *Laminaria hyperborea*, alginate Manugel™ DMB (DMB) derived from *Laminaria hyperborea*, Keltone™ HVCR (HVCR) derived from *Macrocystis pyrifera*, and Keltone™ LV (LV) derived from *Macrocystis pyrifera*.

In the above preferred embodiment of the process of the invention, when the polysaccharide is alginate, the preferred final solutions containing alginates with or without cross-linker that are subjected to the gelation step (b) are the following: (i) LF 120 alginate 1% w/v without cross-Linker; (ii) LF 120 alginate 1% w/v and Ca-Gl 0.1% w/v; (iii) LF 120 alginate 1% w/v and Ca-Gl 0.2% w/v; (iv) LF 120 alginate 1% w/v and $SrCl_2$ 0.15% w/v; (v) LF 120 alginate 1% w/v and $CaCl_2$ 0.1% w/v; (vi) LF 120 alginate 0.5% w/v and Ca-Gl 0.2% w/v; (vii) LF 20/60 alginate 1% w/v and Ca-Gl 0.2% w/v; (viii) HVCR alginate 0.5% w/v and Ca-Gl 0.2% w/v; and (ix) HVCR alginate 1% w/v and Ca-Gl 0.2% w/v.

The freezing step (c) of the process of the invention may be by rapid freezing in a liquid nitrogen bath at about −80° C. for about 15 minutes, or by slow freezing in a freezer at about −18° C. for about 8 to 24 hours. The most preferred means of freezing is by rapid freezing in a liquid nitrogen bath as noted above.

The drying step (d) is preferably by way of lyophilization under conditions of about 0.007 mmHg pressure and at about −60° C.

For the purposes of preparing the polysaccharide sponges of the invention with various shapes and sizes, for example, nose shapes, cube shapes, cylindrical shapes and the like (see FIG. 2), it is preferable to carry out the process of the invention by pouring the initial polysaccharide solution into an appropriately shaped vessel having the desired shape and performing the gelation and subsequent steps of the process in this shaped vessel.

The present invention also provides an polysaccharide sponge of the invention, in particular alginate sponges, as noted above for use as a matrix, substrate or scaffold for growing mammalian cells in vitro. Another preferred use of the polysaccharide sponges of the invention is their use as a matrix substrate or scaffold for implantation into a patient to replace or repair tissue that has been removed or damaged, wherein said implanted sponge is a substrate, matrix or scaffold for surrounding tissue to invade it, proliferate thereon and replace the damaged or removed tissue, or wherein said implant is an initial substrate for vascularization by the surrounding host tissue and the vascularized implant then serves as a substrate to receive injected cells of choice from the host or grown in vitro, said injected cells being capable of rapid acclimitization and proliferation on the vascularized sponge to rapidly replace the damaged or removed tissue.

Yet another preferred use of the polysaccharide sponges of the invention is the use as an implanted support for therapeutic drug delivery into a desired tissue, said drug delivery being by way of the action of genetically engineered cells or natural cells carried by said sponge and expressing said therapeutic drugs, said cells expressing said drug or expressing regulatory proteins to direct the production of the drug endogenously in said tissue. In this preferred use, the therapeutic drug expressed by the cells carried on or in the sponge is a therapeutic protein wherein said cells express said protein or express regulatory proteins to direct the production of said protein endogenously in the tissue into which said sponge is implanted.

Other preferred embodiments for the use of the polysaccharide sponges in accordance with the present invention include: the use of the sponges as a matrix, substrate or scaffold for vitro culturing of plant cells and algae; for use as a matrix, substrate or scaffold for the delivery to a tissue or organ of genetically engineered viral vectors, non-viral vectors, polymeric microspheres and liposomes all encoring or containing a therapeutic agent for said tissue or organ; for use as a matrix, substrate or scaffold for in vitro fertilization of mammallian oocytes; for use as a matrix, substrate or scaffold for storage of fertilized mammalian oocytes, or other mammalian cells cultured in vitro; for use as a matrix, substrate or scaffold for the storage of plant cells and algae cultured in vitro; and for use as a matrix, substrate or scaffold for the transplantation of cells grown on or within the sponge in vitro into a tissue of a patient in need of the cells as a result of tissue damage, removal or dysfunction.

Preferred uses of the polysaccharide sponge of the invention as noted above include the use thereof for growing fibroblast cells in vitro; and for growing hepatocyte cells in vitro. In accordance with these preferred uses, the polysaccharide sponges of the invention may be used as transplantation devices to transplant fibroblast cells to replace damaged or removed skin tissue, or for the transplantion of hepatocytes to replace damaged or removed liver tissue.

The present invention thus also provides artificial organ equivalents which serve to provide the essential function of the organ which they are to replace fully or partially or whose function they are designed to augment. The artificial organ equivalents of the invention therefore comprise a polysaccharide sponge of the invention, as noted above, and representative cells of the said organ, the cells having been grown on or within the sponge in vitro to the stage wherein they are fully active and equivalent to the active cells of the organ and thereby the artificial organ is suitable for transplantation or implantation in all the various ways thereof as detailed above, into a patient in need thereof following organ damage, removal or dysfunction. Preferred embodiments of the artificial organ equivalents of the invention being artificial skin comprising a polysaccharide sponge of the invention and dermal fibroblast cells, as well as an artificial liver equivalent comprising a polysaccharide sponge of the invention and hepatocytes.

BRIEF DESCRIPTION OF THE DRAWINGS

a) LF120, 1% (w/v) (no crosslinker)
b) LF120, 1% (w/v)+0.1% (w/v) Ca-Gl
c) LF120, 1% (w/v)+0.2% (w/v) Ca-Gl
d) LF120, 1% (w/v)+0.15% (w/v) $SrCl_2$
e) LF120, 1% (w/v)+0.1% (w/v) $CaCl_2$
f) LF20/60, 1% (w/v)+0.2% (w/v) Ca-Gl
g) LF120, 0.5% (w/v)+0.2% (w/v) Ca-Gl
h) HVCR, 0.5% (w/v)+0.2% (w/v) Ca-Gl
i) HVCR, 1% (w/v)+0.2% (w/v) Ca-Gl
j) LF 120, 0.5% (w/v)+0.2% (w/v) Ca-Gl, Freezer
k) LF 120, 1% (w/v)+0.2% (w/v) Ca-Gl, Freezer

Figure 5:
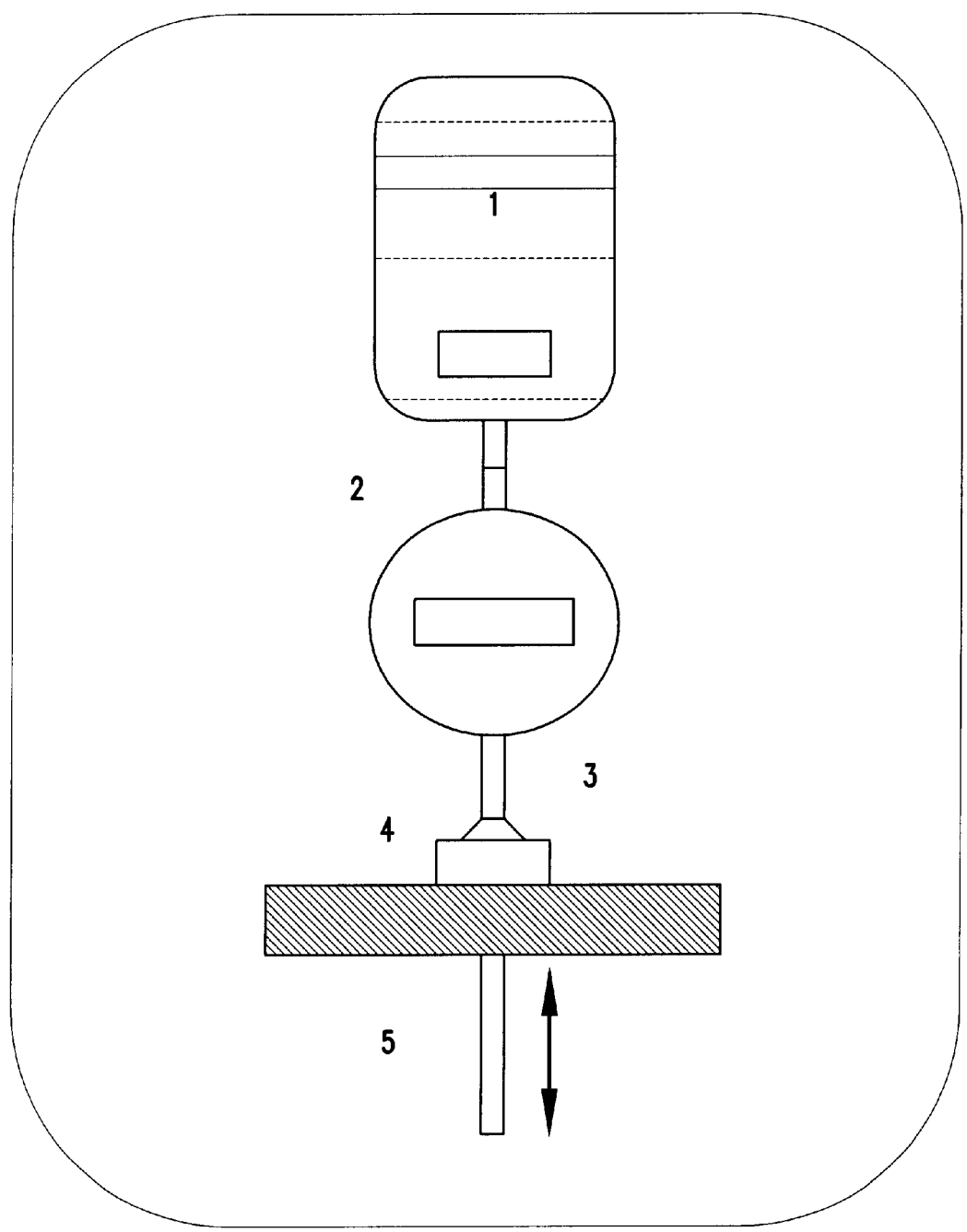
Figure 6:
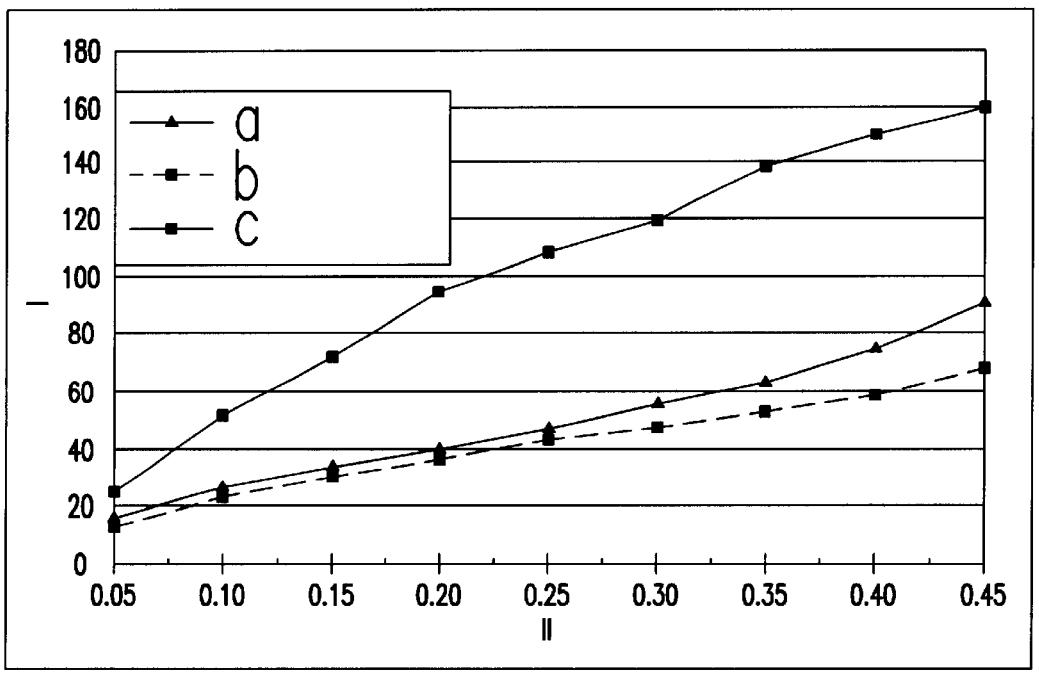
Figure 7:
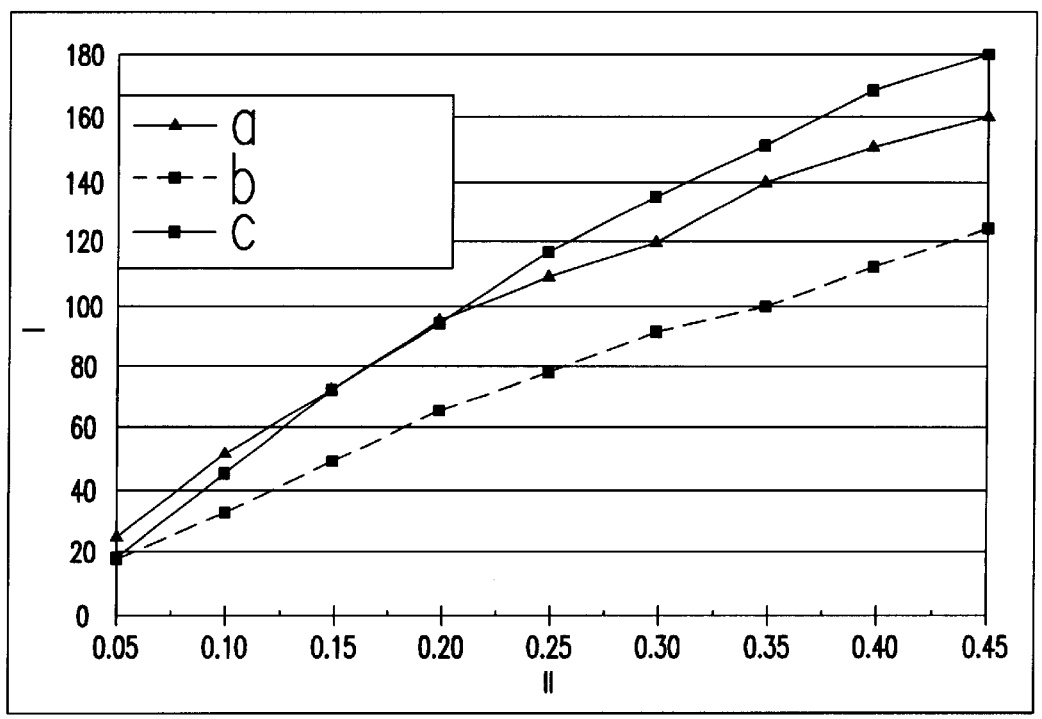
Figure 8:
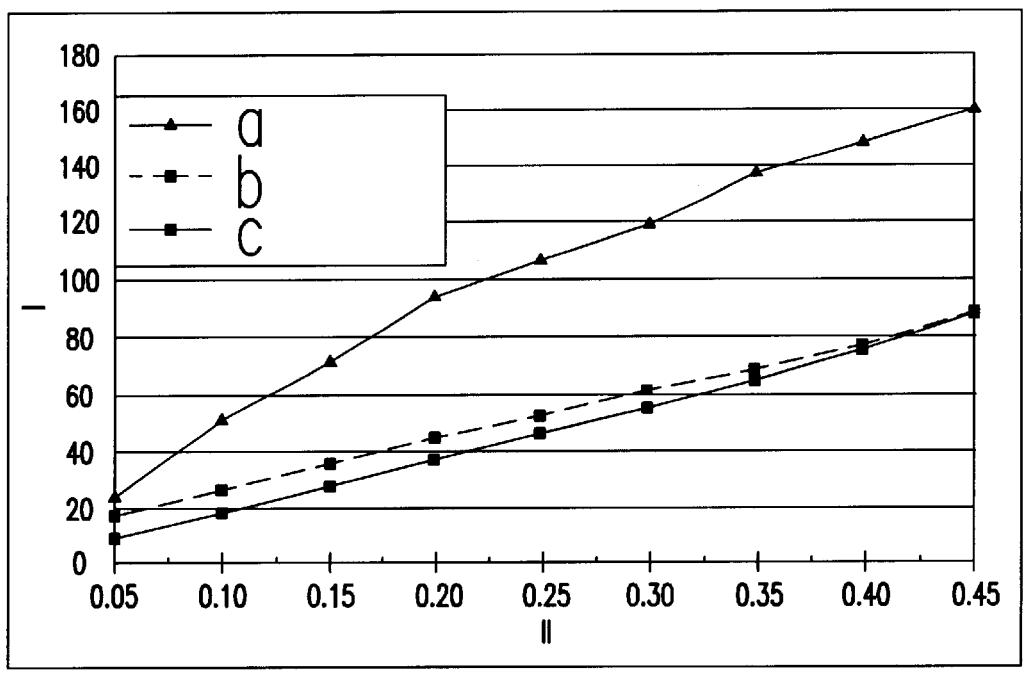
Figure 9:
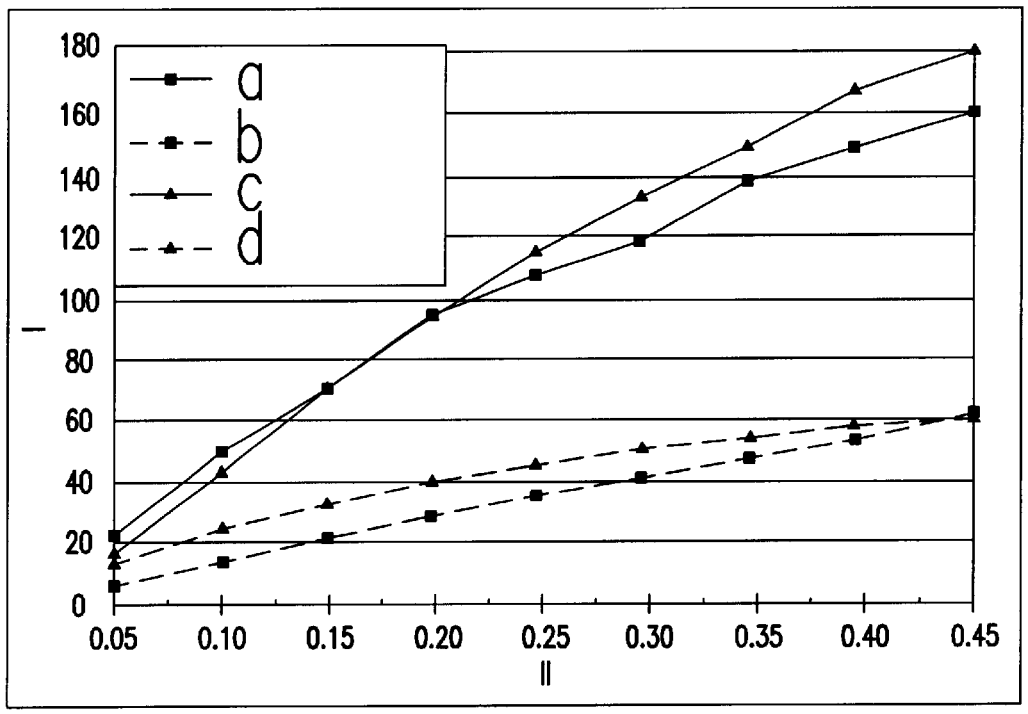
Figure 10:
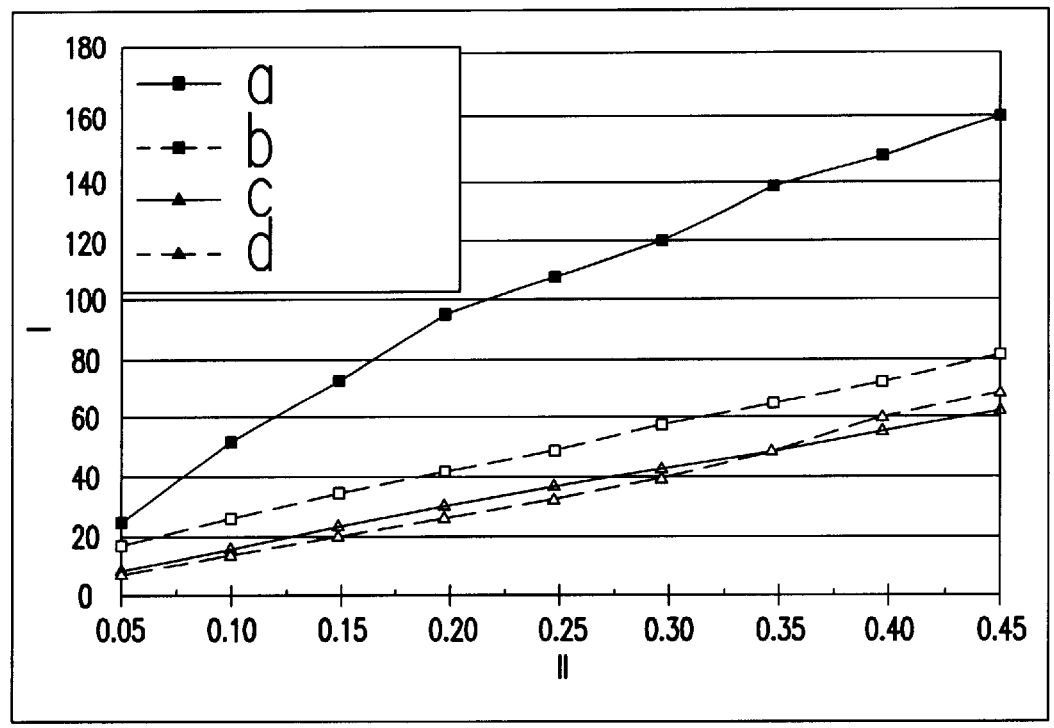
Figure 11:
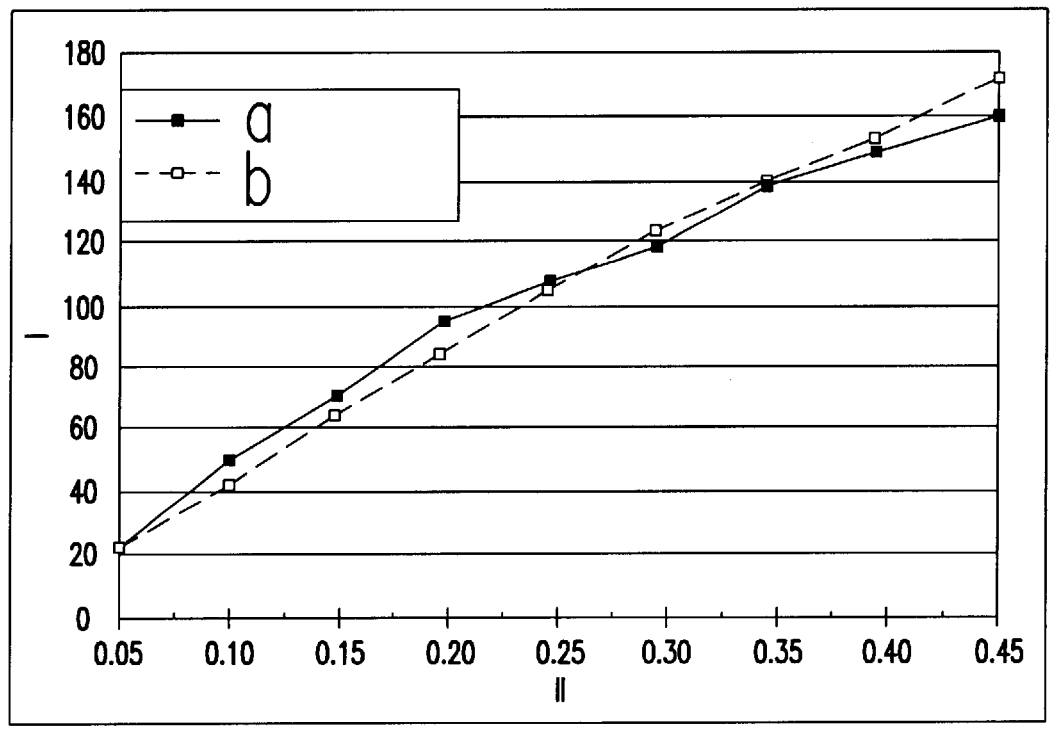
Figure 12:
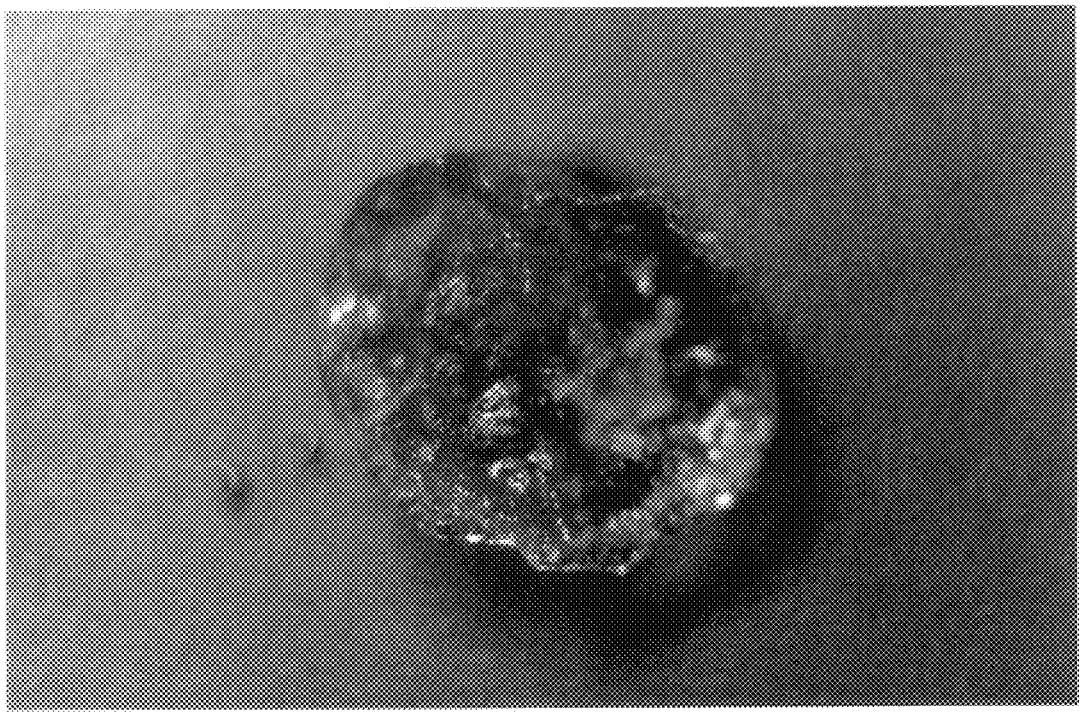
Figure 13:
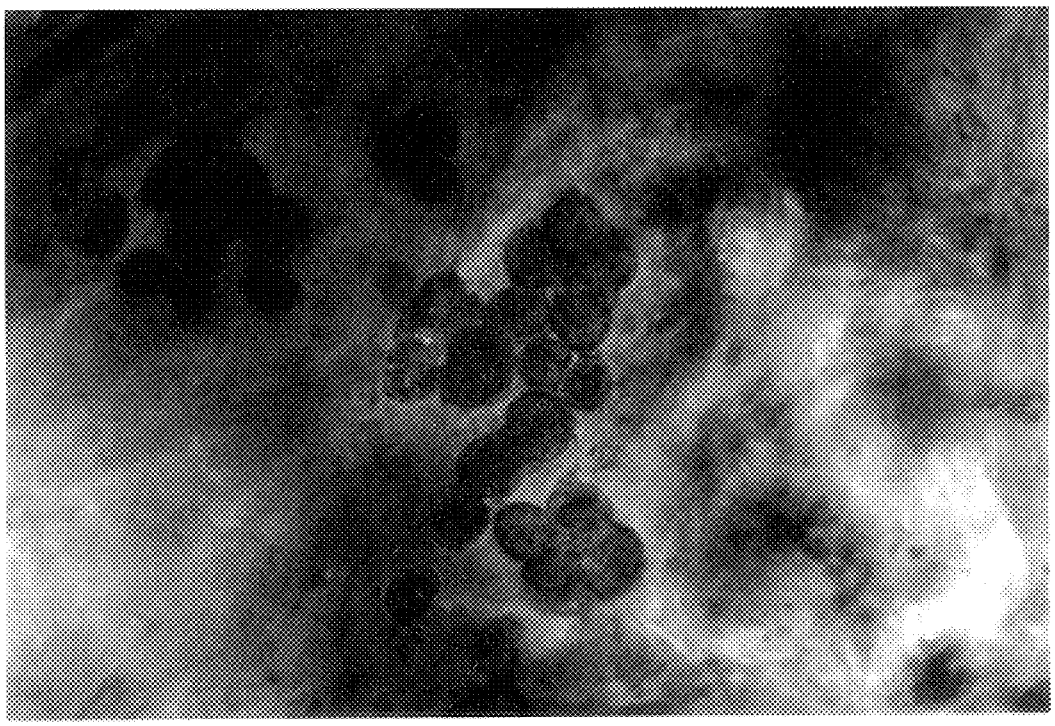
Figure 13:
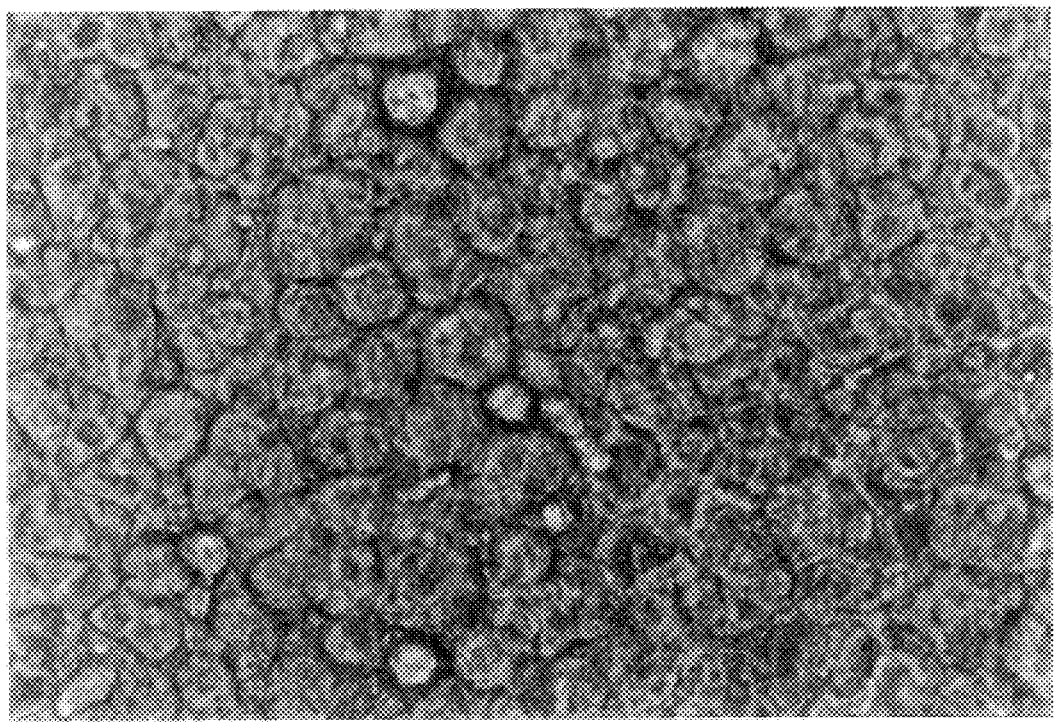
Figure 14:
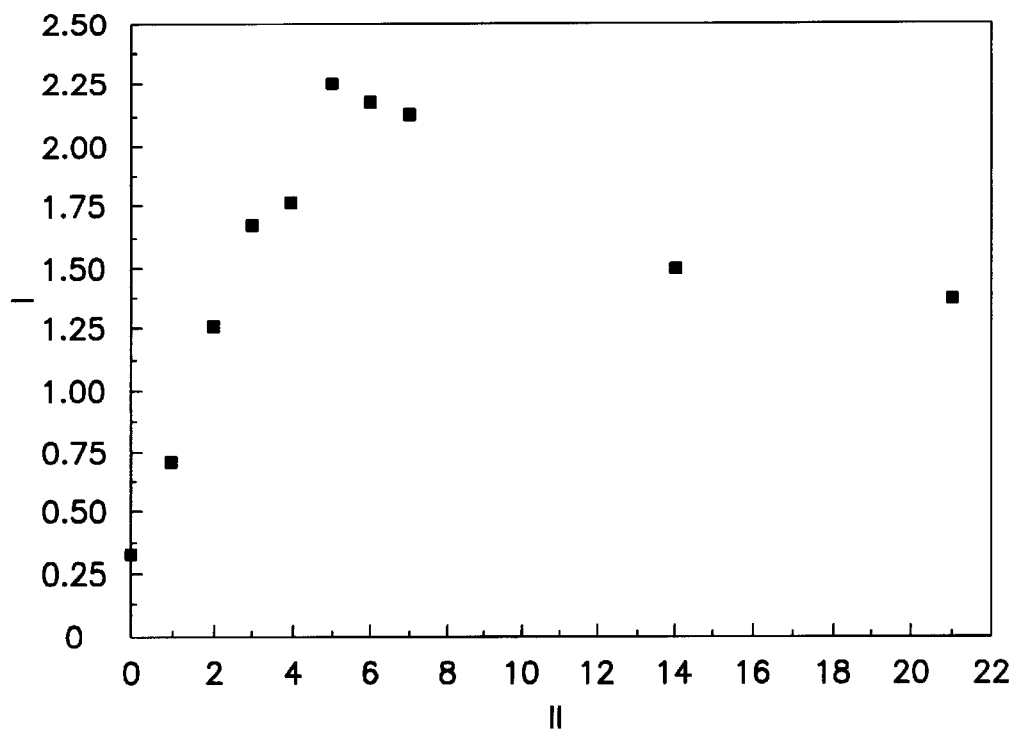
Figure 15:
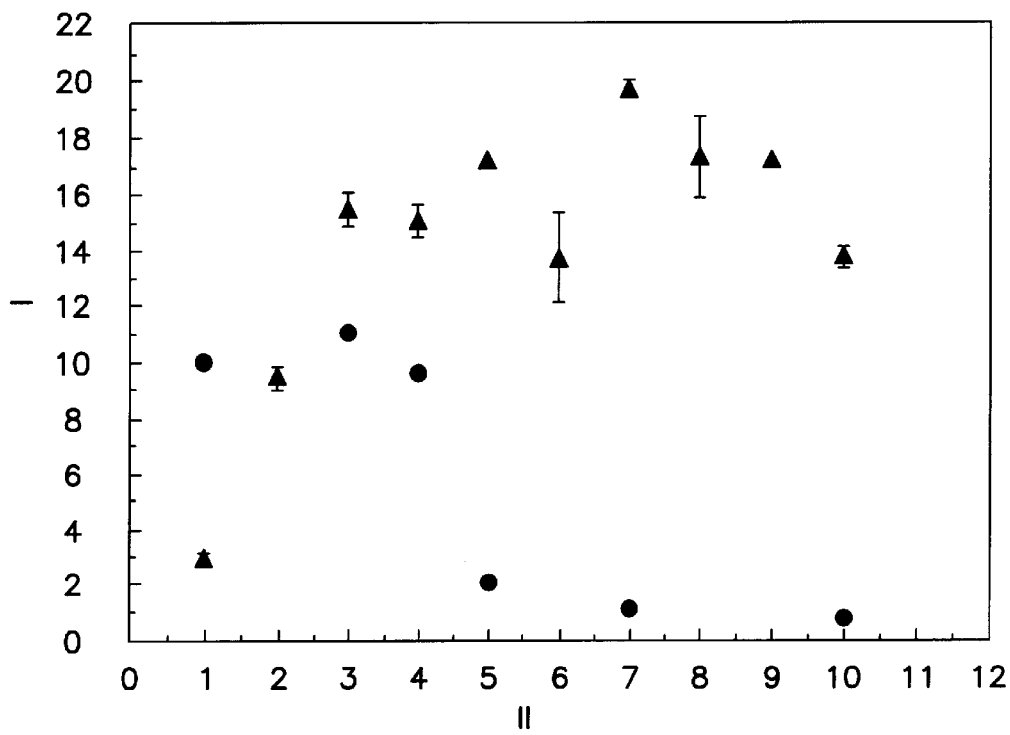

4a): 1, LF 120, 1% (w/v) (no crosslinker) 2, LF 120, 1% (w/v)+0.1% (w/v) Ca-Gl 3, LF 120, 1% (w/v)+0.2% (w/v) Ca-Gl 4b): 1, LF 120, 1% (w/v)+0.2% (w/v) Ca-Gl 2, LF 120, 1% (w/v)+0.1% (w/v) CaCls 3, LF 120, 1% (w/v)+0.15% (w/v) $SrCl_2$ 4, LF 20/60, 1% (w/v)+0.2% (w/v) Ca-Gl 4c): 1, LF 120, 1% (w/v)+0.2% (w/v) Ca-Gl (Freezer) 2, LF 120, 0.5% (w/v)+0.2% (w/v) Ca-Gl (Freezer) 3, LF 120, 1% (w/v)+0.2% (w/v) Ca-Gl 4, LF 120, 0.5%(w/v)+0.2% (w/v) Ca-Gl 4d): 1, LF 120, 1% (w/v)+0.2% (w/v) Ca-Gl 2, LF 120, 0.5% (w/v)+0.2% (w/v) Ca-Gl 3, HVCR, 1% (w/v)+0.2% (w/v) Ca-Gl 4, HVCR, 0.5% (w/v)+0.2% (w/v) Ca-Gl;

FIG. 5 is a schematic representation of the apparatus used to determine the mechanical properties, in particular the load applied to the sponge versus the compression of the sponge, and thereby provide a means for determining the rigidity of the sponge, as detailed in Example 3. The numbers in the Figure represent the following 1, Load Cell; 2, Deformation Cell; 3, Indentor; 4, Sample; 5, Translation Table;

FIG. 6 depicts a graphical representation of the results showing the effect of the change in the concentration of the cross-linker calcium gluconate (Ca-Gl) on the compressibility of alginate sponges as detailed in Example 3. Ordinate (I): stress [kPa]; Abscissa (II): strain. The letter N indicates freezing the gels by liquid nitrogen.

a) (triangles): LrF 120 1% (w/v), no crosslinker, N
b) (squares, dotted line): LF 120 1% (w/v)+0.1% (w/v) Ca-Gl, N
c) (squares, solid line): LF 120 1% (w/v)+0.2% (w/v) Ca-Gl, N FIG. 7 depicts graphically the results showing the effect of the relative amount of guluronic (G) acid residues in the alginates and the viscosity of the alginate solution on the compressibility of the alginate sponges prepared therefrom, as detailed in Example 3. Ordinate (I): stress [kPa], Abscissa (II): strain. Hereinafter, the letter N indicates freezing the gels by liquid nitrogen.

a) (triangles): LF 120, 1% (w/v)+0.2% (w/v)Ca-Gl, N
b) (squares, dotted line): LF 20/60, 1% (w/v)+0.2% (w/v) Ca-Gl, N
c) (squares, solid line): HVCR 1%+0.2% (w/v) Ca-Gl, N FIG. 8 depicts graphically the results showing the effect of different cross-linkers used in the preparation of the alternate sponges on the compressibility of the alginate sponges produced therewith, as detailed in Example 3. Ordinate (I): stress [kPa], Abscissa (II): strain.

a) (triangles): LF 120, 1% (w/v)+0.01M Ca-Gl, N
b) (squares, dotted line): LF 120, 1% (w/v)+0.01M $CaCl_2$, N
c) (squares, solid line): LF 120, 1% (w/v)+0.01M $SrCl_2$, N FIG. 9 depicts graphically the results showing the effects or the alginate concentration on the compressibility of alginate sponges prepared therewith, as detailed in Example 3. Ordinate (I): stress [kPa], Abscissa (II): strain.

a) (squares, solid line): LF 120 1% (w/v)+0.2% (w/v) Ca-Gl, N
b) (squares, dotted line): LF 120 0.5% (w/v)+0.2% (w/v) Ca-Gl, N
c) (triangles, solid line): HVCR 1% (w/v)+0.2% (w/v) Ca-Gl, N
d) (triangles, dotted line): HVCR 0.5% (w/v)+0.2% (w/v) Ca-Gl, N FIG. 10 depicts graphically the results showing the effect of the freezing rate during the preparation of the alginate sponges on the compressibility of the so-produced alginate sponges, as detailed in Example 3. Ordinate (I): stress [kPa], Abscissa (II): strain. The letters F and N indicate that the gels were frozen in freezer and liquid nitrogen, respectively:

a) (squares, solid line): LF 120 1% (w/v)+0.2% (w/v) Ca-Gl, N
b) (squares, dotted line): LF 120 1% (w/v)+0.2% (w/v) Ca-Gl, F
c) (triangles, solid line): LF 120 0.5% (w/v)+0.2% (w/v) Ca-Gl, N
d) (triangles, dotted line): LF 120 0.5% (w/v)+0.2% (w/v) Ca-Gl,F FIG. 11 depicts graphically the results showing the effect of gas sterilization of the alginate sponges on the compressibility of so-sterilized sponges, as detailed in Example 3. Ordinate (I): stress [kPa], Abscissa (II): strain. "Gas" in b) represents sterilization of the alginate product by gas.

a) (squares, solid line): LF 120 1% (w/v)+0.2% (w/v) Ca-Gl, N b) (squares, dotted line): LF 120 1% (w/v)+0.2% (w/v) Ca-Gl, N, Gas FIG. 12 is a reproduction of a light micrograph showing sponges seeded with fibroblast and cultured over a long period at 37° C. (one month), indicative of the stability of the sponges for prolonged periods in cluture, as detailed in Example. 4;

FIG. 13 shows two reproductions of light micrographs at 100×magnification of the top view of the sponge surface (upper micrograph) and of the cross-section within the sponge (Gower magnification) five days after incubating the sponge with the cells, as detailed in Example 5;

FIG. 14 depicts a graphical representation of the results showing the proliferation of hepatocytes seeded in alginate sponges over a prolonged period of time in culture (3 weeks) as detailed in Example 5. Ordinate (I): cell concentration [$10^6$ cells/ml]; Abscissa (II): time [days];

FIG. 15 depicts graphically the comparative results showing the rate of albumin secretion from hepatocytes seeded in alginate sponges versus hepatocytes grown on collagen I gels in vitro over a period of ten days, as detailed in Example 5. Ordinate (I): $\mu$g antibody/(day*$10^6$ cells); Abscissa (II): time [days]. Circles represent results obtained on collagen type I; triangles represent results obtained in sponges.

Figure 16:
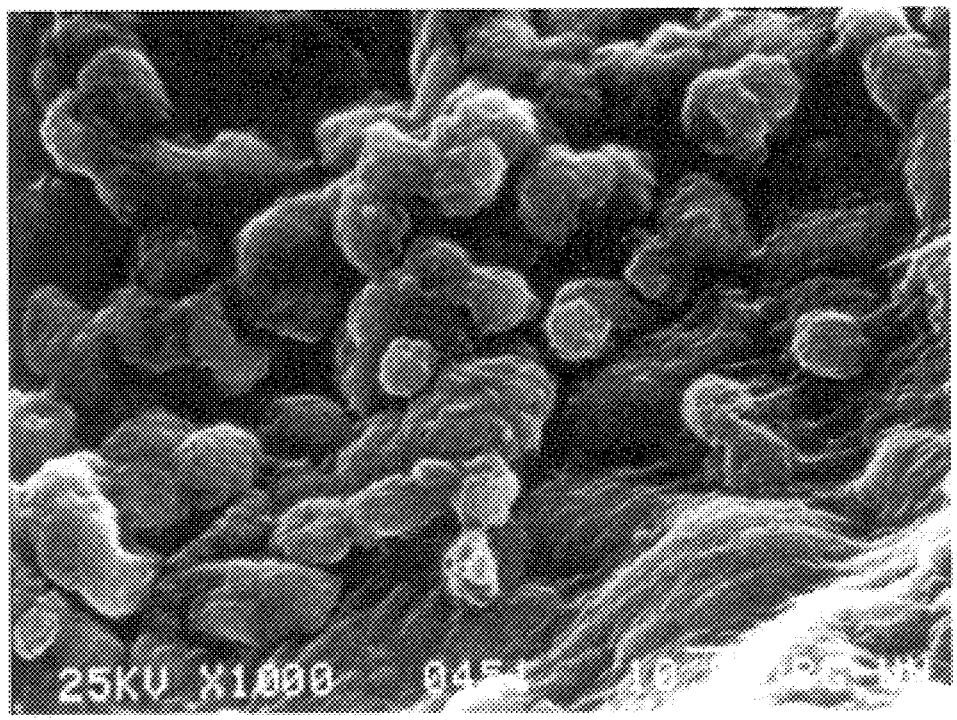
Figure 16:
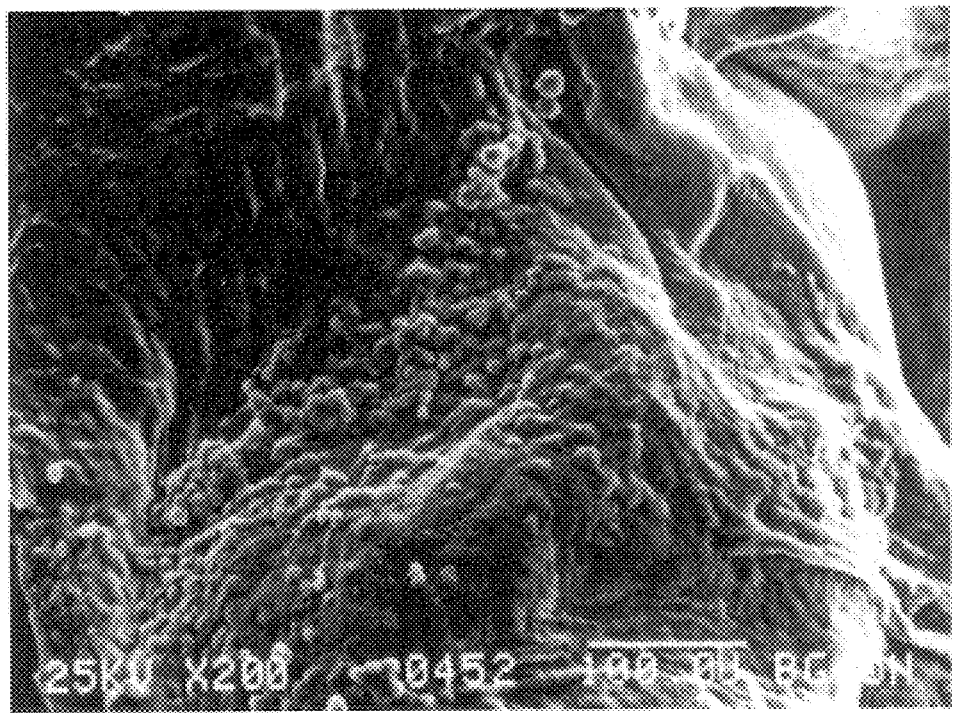
Figure 17:
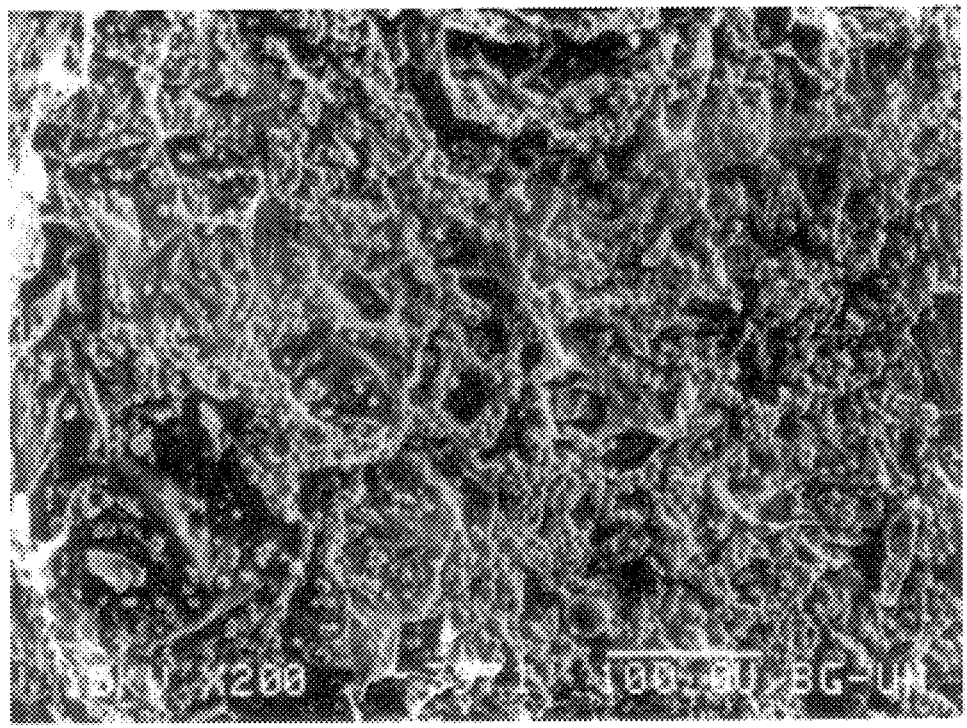
Figure 17:
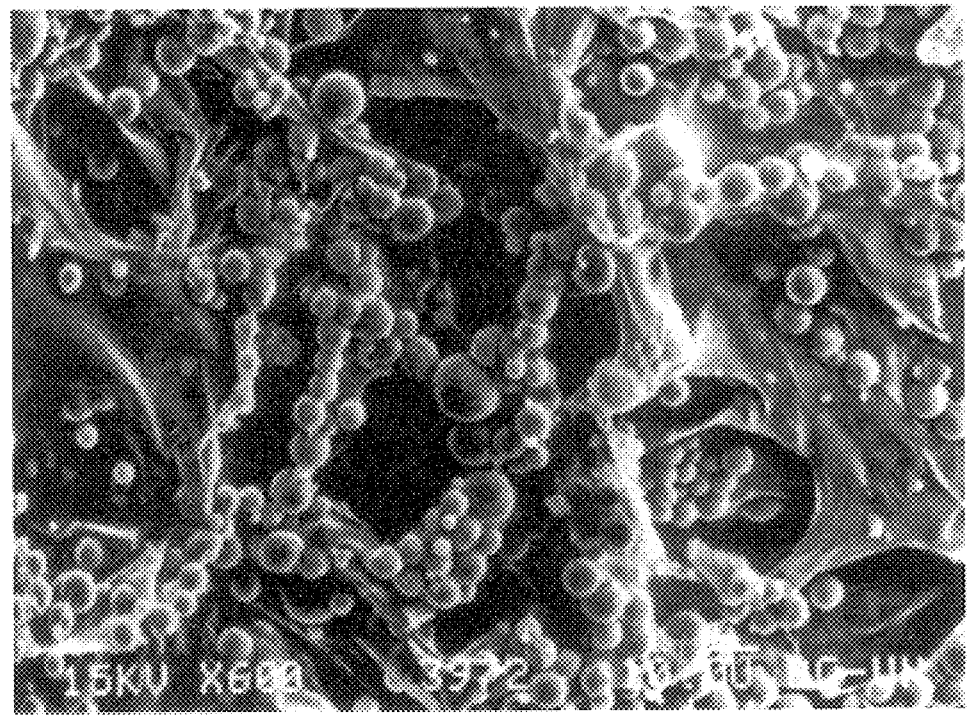

FIG. 16 shows reproductions of SEM micrographs at a higher (top micrograph) and lower (bottom micrograph) magnifications in which fibroblasts are observable growing actively within fibroblast seeded sponges five days after culture in vitro as detailed in Example 6;

FIG. 17 shows reproductions of SEM micrographs at higher bottom micrograph) and lower (top micrograph) magnifications in which are observable protein-containing microspheres within the pores of an alginate sponge, as described in Example 7.

DETAILED DESCRIPTION OF THE INVENTION

As set forth hereinabove and as detailed hereinbelow, the present invention concerns new polysaccharide sponges characterized prima-by their morphology and mechanical properties, as well as their stability in prolonged culture, as well as a new method for the preparation of these polysaccharide sponges. The polysaccharide sponges of the present invention are particularly useful for growing various mammalian cells in vitro and for use in implantations and transplantations in a number of various ways as detailed above, into patients in need thereof, following tissue damage, removal or dysfunction. For example, the alginate sponges of the invention have been shown in accordance with the present invention to be capable of supporting the growth, proliferation and biological function of hepatocytes and hence sponges seeded with such hepatocytes may be used for liver cell transplants, and likewise, the sponges are also capable of supporting the growth, proliferation and biological function of fibroblasts and hence may also be used for skin (dermis) transplants As mentioned above, the previously known porous absorbable matrices fabricated from various natural and synthetic polymers and intended for use as supports or matrices for implants to facilitate the regeneration of tissue when required following disease, trauma or reconstructive surgical procedures, have a number of drawbacks which has prevented their being used on a wide scale for the above medical applications. These drawbacks include the following: many of the previous polymeric matrices only provide for the growth of thin layers of cells and hence are limited to applications, for example, the growing of thin layers of fibroblast cells for skin cells, these matrices not being adequate to support the growth of thicker layers of cells or aggregates of cells, for example, the growth of hepatocytes, and hence, cannot be used effectively for transplantation of such types of cells. Further, in many of the previously developed porous matrices designed for use as implants or substrates for transplants have accordingly been designed such that they are biodegradable, but, however, it has been observed that, for example, the collagen-based matrices, degrade at a relatively rapid rate and hence when used as supports for transplanted cells, they often degrade before the transplanted cells have had the necessary time to establish themselves in vivo and form the desired new tissue matrix. Even in the case of longer-lasting matrices, it has been noticed that many of them give rise to undesirable side effects in vivo, for example, many are immunogenic, many become contracted and rigid, making them less amenable to surgical handling, many give rise to undesirable degradation products when they biodegrade, and very often the morphology of these matrices is such that the cells carried with the matrix are not sufficiently supplied with necessary nutrients to support their long-term growth, as the porous nature of these matrices is such that the free flow of nutrients in and out of the matrix is limited or restricted, or does not support vascularization into the matrix from the surrounding tissue into which the matrix was implanted.

The polysaccharide sponges of the present invention address and overcome all of the above drawbacks of the previously known porous matrices As mentioned above, the polysaccharide sponges of the present invention may comprise many different kinds of polysaccharides, for example the polyanionic polysaccharides such as alginates, gellan, gellan gum, xanthan chitosan, agar, carrageenan and the polycationic polysaccharides such as chitosan. Of these polysaccharides, the preferred ones are the above-mentioned alginates, which come in various forms. Hence, the preferred sponges of the present invention are composed of alginate, which represents a family of polyanionic copolymers derived from brown sea algae comprising 1,4-linked β-D-mannuronic (M) and α-L-guluronic (G) acid residues in varying proportions. Alginate is soluble in aqueous solutions at room temperature and forms stable gels in the presence of certain divalent cations such as calcium, barium, and strontium, as well as in the absence of such cations under certain conditions such as, for example, reduced pH or special processing conditions as detailed herein. Further, the unique properties of alginate combined with its biocompatibilty (see Sennerby et al. 1987 and Cohen et al., 1991) and relatively low cost have made alginate an important polymer in medicinal and pharmaceutical applications (for example, wound dressings and dental impression material). Moreover, alginate has already been approved by a large number of regulatory authorities as an acceptable wound dressing and as food additives.

Moreover, alginates are commercially available from a number of manufacturers (see Table 1) to produce the alginates according to stringent pharmaceutical requirements set by the European and U.S. pharmacopeas (pharmaceutical regulatory bodies).

Use of various types of alginates in accordance with the present invention to prepare the various sponges of the invention has provided a range of sponges, each being a highly porous matrix which supports the growth, proliferation and biological function of a wide range of cells, including cells such as hepatocytes, which grow in aggregates or thick layers. These porous sponges are also capable of ensuring an adequate supply of nutrients to the cells grown therein and are amenable to the invasion of blood vessels, i.e., when implanted or transplanted in vivo they are amenable to vascularization. Further, in view of the fact that the alginate is a hydrophilic polymer, the alginate sponges of the present invention are easily wetted, allowing for a more efficient penetration of cells into the matrix during seeding. It should be noted that in previous efforts to use alginates for cell transplantations, it was primarily sought the development of a semi-permeable membrane made of the alginates for the purpose of protecting the cells encased by this membrane from the host immune system (see, for example, King et al., 1987 and Sun et al., 1987). This approach, thus, essentially provided alginate beads which were coated by a semi-permeable membrane, for example, by absorbing to the alginate beads a polycation such as polylysine, which however resulted in a great reduction of the beads' or microcapsules' permeability towards nutrients which subsequently leads to cell death of the cells encapsulated within these alginate beads or microcapsules.

In contrast, as noted above, the alginate sponges of the present invention are fully amenable to the flow of nutrients into the sponge malls and also amenable to vascularization in vivo.

As will be detailed hereinbelow in the examples, the porosity and sponge morphology (pore size and distribution) of the polysaccharide, for example, the alginate sponges of the invention are dependent on various formulation and processing parameters, which may be easily controlled in the process of the invention and allows for the obtention of a wide range of macroporous sponges suitable for cell culture, implantation and transplantation. All of these sponges have good mechanical properties, and are suitable for supporting the growth and proliferation of various mammalian cells, for example, fibroblasts and hepatocytes, and are therefore applicable for providing at least a temporary support for these cells when used, for example, for transplantations to replace skin or liver tissue.

As mentioned hereinabove, the sponges of the present invention have a very wide range of uses, for example, they may also be used for the in vitro culturing of plant cells and algal cells, in particular the microalgae; for the in vitro support of mammalian oocytes for the purposes of in vitro fertilization of these oocytes, and hence also for the storage of these plant cells, algae, and fertilized oocytes, in view of the fact that the polysaccharide sponges of the invention, in particular the alginate sponges, may be frozen with great efficiency to about −18° C. (liquid nitrogen), and when thawed, the sponges provide a very suitable matrix for the protection and renewed proliferation of such stored cells. Moreover, as mentioned above, the sponges of the invention may also be used as drug delivery vehicles, either by way of carrying genetically engineered or natural cells which produce a desired product or drug which is produced in these cells and released to the host from the site at which the sponge was implanted, or the cells are capable of producing and releasing to the surrounding tissue one or more regulatory proteins which direct the production of a desired cellular product in the cells of the tissue surrounding the implant. Likewise, the sponges of the invention may also be used to deliver various viral vectors, non-viral vectors, polymeric microspheres (see Example 7), liposomes, which either encode or contain therapeutic products or drugs of choice that it is desired to administer to the host tissue or organ in which the implant is placed. All of these viral vectors, non-viral vectors, polymeric microspheres and liposomes may be prepared as are well documented in the art to encode or to contain a very wide range of desired therapeutic agents, for example, various enzymes, hormones and the like, and may be inserted into the sponges at the time of preparation of the sponge or following the preparation of the sponge. For example, as is detailed in Example 7, it is possible to encapsulate protein-containing microspheres within alginate sponges by adding such microspheres within alginate sponges by adding such microspheres to the alginate solution at the time of adding the cross-linker at the stage of gelation of the alginate solution in accordance with the process of the invention. The resulting alginate gels containing such microspheres are then processed into sponges containing the same by the freezing and lyophilization steps of the process of the present invention. Hence, the sponges of the invention are also readily useful for the delivery of agents, which are usually not suitable for such porous materials, by way of introducing such agents in a form, e.g., microspheres, which are retainable within the sponge, and provide for the slow- or controlled-release of the therapeutic agent within the microsphere.

The present invention will be described in more detail in the following non-limiting examples and the accompanying figures:

EXAMPLE 1

Preparation of the Alginate Sponges

As noted above, alginates belong to a family of polyanionic copolymers derived from brown sea algae and comprise 1,4-linked β-Δ-mannuronic (M) and α-L-guluronic (G) acid residues in varying proportions. Alginates are soluble in aqueous solutions at room temperature and form stable gels in the presence of certain divalent cations such as, for example, calcium, barium and strontium.

Alginates, with varying comonomer ratio, i.e., varying content of mannuronic (M) and guluronic (G) acid, and varying viscosity were used in the preparation of the alginate sponges of the present invention. Key properties of these alginates are summarized in Table 1.

TABLE 1

Properties of alginates used in the present invention:

| Alginate Type | [1]M, % | [1]G, % | Viscosity[1], cP (1% w/v, 25° C.) | Source (species of brown sea algae) |
|---|---|---|---|---|
| *Protanal LF 120 | 25–35 | 65–75 | 150–400 | Laminaria hyperborea (stem) |
| *Protanal LF 20/60 | 25–35 | 65–75 | 100–150 | Laminaria hyperborea (stem) |
| •Keltone HVCR | 61 | 39 | 150–400 | Macrocystis pyrifera |
| *MVG | 30 | 70 | 200–800 | Laminaria hyperborea (stem) |
| *Protanal HF 120 | 25–35 | 65–75 | 600–800 | Laminaria hyperborea (stem) |
| *Protanal SF 120 | 25–35 | 65–75 | 400–600 | Laminaria hyperborea (stem) |
| *Protanal SF 200 RB | 55–65 | 35–45 | 400–600 | Laminaria hyperborea (leaves) |

TABLE 1-continued

Properties of alginates used in the present invention:

| Alginate Type | [1]M, % | [1]G, % | Viscosity[1], cP (1% w/v, 25° C.) | Source (species of brown sea algae) |
|---|---|---|---|---|
| *Protanal LF 200 RB | 60–50 | 40–50 | 200–400 | *Laminaria hyperborea* (leaves) |
| •Manugel DMB | 31 | 69 | 200–400 | *Laminaria hyperborea* |
| •Keltone LV | 61 | 39 | 50–150 | *Macrocystis pyrifera* |

*Pronova Biopolymer (Drammen, Norway).
•Kelco, Division of Merck (San Diego, CA).
[1]M and G - mannuronic and guluronic residue content, respectively, in accordance with manufacturer's specification.

It should be noted, that in the following examples and their accompanying figures, relation is made only to the above three first types of alginate as regards the alginate sponges which were prepared therefrom and as regards their various characteristics. All of the remaining types of alginate listed in Table I, although not specifically exemplified, have been used in the preparation of alginate sponges in accordance with the present invention, all providing sponges of the desired characteristics and properties (results not shown).

For the preparation of the various alginate sponges of the invention, various cross-linking agents (cross-linkers) were used in varying concentrations of cross-linker solution. These are summarized in Table 2.

TABLE 2

The different cross-linkers and cross-linker solution concentrations used in accordance with the present invention:

| | Concentration, % (w/v) | | | |
|---|---|---|---|---|
| Crosslinker | 0.01 | 0.2 | 0.3 | 0.4 |
| Calcium chloride | *+(10 mM) | +(15 mM) | +(20 mM) | |
| Strontium chloride | | *+(10 mM) | | |
| Calcium gluconate | +(5 mM) | | *+(10 mM) | +(15 mM) |

*These concentrations are equivalent to 10 mM, and likewise there is shown in 2 the mM concentrations of the various cross-linkers in each cross-linker solution prepared.

It should be noted that many other cross-linking agents are also suitable for the preparation of the alginate sponges, of which the above three listed in Table 2 represent just an example. It has been found that cross-linking agents of a wide variety, such as the salts of calcium, copper, aluminum, magnesium, strontium, barium, tin, zinc, chromium, organic cations, poly(amino acids), poly(ethyleneimine), poly (vinylamine), poly(allylamine) and polysaccharides are all suitable for the preparation of the sponges of the present invention. Thus, while in the following examples and the accompanying figures there is exemplified only sponges made with the above specific cross-linkers of Table 2, the other above-noted cross-linking agents have also been used successfully (results not shown).

Stock solutions of sodium alginate, at concentrations of 1–3% (w/v), were prepared by dissolving the polymer powder in double-distilled water and mixing using a homogenizer with dispenser tool 10G (Heidolph Elektro Kelheim, Germany) at 25,000 RPM, for 30 min, at room temperature.

Figure 1:
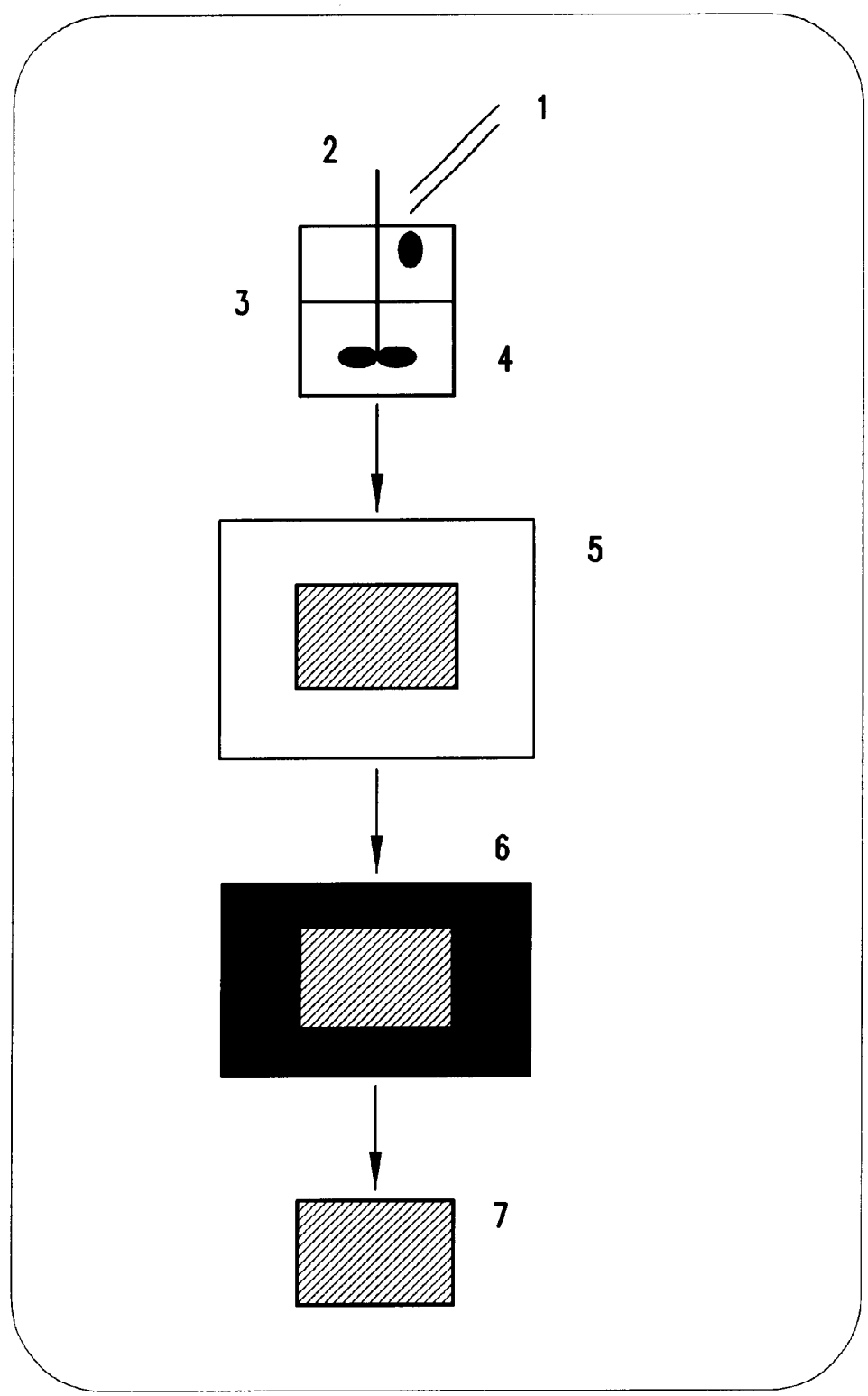
FIG. 1 depicts a schematic representation of the general procedure for the preparation of alginate sponges in accordance with the invention, as set forth in detail in Example 1; The numbers in the figure represent the following: 1, Cross-linker Solution; 2, Mixer; 3, Alginate Solution; 4, Geletion; 5, Freezing; 6, Lyophilization; 7, Alginate Sponge.

In accordance with the present invention, there has been developed a method for sponge preparation based on 3 steps: (i) gelation of an alginate solution to form a cross-linked hydrogel; (ii) freezing, and (iii) drying by lyophilization. The scheme of sponge preparation is set forth in FIG. 1, a schematic representation of the general procedure for alginate sponge preparation. Briefly, 0.5–1 mL of alginate stock solution, 2% w/v, were poured into the wells of a 24-well plate (well size: 16 mm diameter, 20 mm height), diluted to the desired final concentration with double distilled water, and then cross-linked to form a gel by adding from the cross-linker solution very slowly, while stirring intensively using the homogenizer (Dispenser tool 6G at speed of 31,800 RPM) for 3 min.

The above alginate gels ate then frozen. Two sets of conditions were employed to examine the effect of the speed of freezing on sponge morphology and mechanical properties: 1) by placing the plates on a shelf in a freezer, at between –18° C. and –20° C., overnight; and 2) in a liquid nitrogen bath for 15 min. The frozen gels were lyophilized (Freeze Dry systems LABCONCO Co., Kansas City) at 0.007 mm Hg and a freeze-drying temperature of –60° C.

For tissue culture, the sponges were sterilized by ethylene oxide gas treatment, using a standard ethylene oxide sterilization apparatus. Briefly, the samples were exposed to 100% ethylene oxide atmosphere at a relative humidity of 70% for 3.5 h at 55° C. The samples were then aerated with warm all flow at atmospheric pressure for at least 48 hours to remove residual ethylene oxide from the alginate sponge, and the so-sterilized sponges were stored in laminated bags, at room temperature, until use.

The above technology of aluminate sponge preparation involving the three different steps is of such a nature that each of these steps can influence the morphology, microstructure and mechanical properties of the resultant matrix. Hence, as is detailed in the following examples, the effect of varying these steps was examined with the aim of obtaining an alienate sponge that will be most suitable for cell and tissue transplantation. Hence, the above methodology is the general one for alginate sponge preparation, while the more specific ones are detailed below.

EXAMPLE 2

Morphology of Alginate Sponges

The morphology of the alginate sponges was investigated by scanning electron microscopy (SEM, JEOL JSM-35CF). Samples of the various alginate sponges were mounted on aluminum stubs and coated with an ultrathin (100 Å) layer of gold in a Polaron E 5100 coating apparatus. The parameters of the sponge microstructure were investigated by geometrical measurements on the SEM-micrographs. The pore length, width and wall thickness (i.e., the average distance between neighboring pores), were measured by a stereo microscope (Bausch & Lomb) equipped with an optical micrometer. The effective size of the pores was calculated, using the equation:

$$d=\sqrt{l \cdot h}$$

where l, h—are the average length and width of the pores, respectively. Wall thickness measurements were performed as this parameter characterizes the distance between the pores, and hence the microstructure of the sponges.

Figure 2:
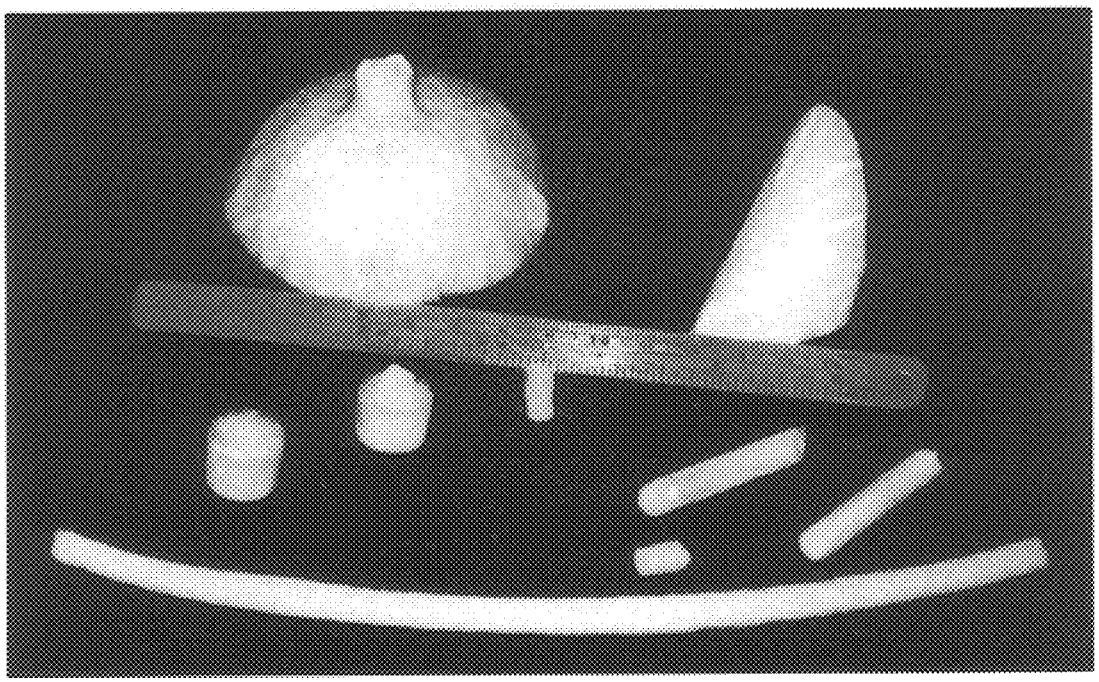
FIG. 2 is a reproduction of a photograph illustrating the various shapes and sizes of alginate sponges which may be produced in accordance with the invention, as detailed in Example 2.

Initially, the shape of the sponges was determined by the dish in which the processing of the sponge was carried out. Thus, sponges with various shapes, for example, a nose-shaped, tube-shaped and cylinder shape, as well as many others, were easily constructed by simply choosing the appropriate vessels in which to prepare and process the sponges. Examples of various sponges of different shapes are shown in FIG. 2, which is a reproduction of a photograph showing nose-shaped, tube-shaped and cylindrical-shaped sponges. In FIG. 2, there is also shown a ruler to provide an indication of the sizes (lengths, widths) of the various sponges in centimeters/inches. As illustrated in FIG. 2, the various preferred sponges of the invention are those having rounded edges, this being the preferred geometry when compared to previously known implant matrices which had sharp angles or edges that are undesirable in view of it having been shown that such sharp implants may induce the greatest inflammatory response (see, for example, Matlaga et al., 1976).

Using the above-noted methodology for the preparation of the alginate sponges of the present invention, there has been obtained highly porous, well interconnected sponges having a typical organization of the polymeric material. The morphology of the alginate sponges, in terms of pore size, number and distribution, as well as the distance between the pores, i.e., the wall thickness, was shown to be in accordance with the present invention, to be highly dependent on the concentration and type of cross-linker and the initial concentration of the alginate solution used in the preparation of the sponges. The most dense structure with the smallest number of pores per cubic cm ($cm^3$) and the largest wall thickness was obtained in sponges that were produced by the freeze-drying procedure with no cross-linker added during processing. The surface morphology by SEM of various sponges prepared using the various kinds of alginates, at various concentrations, with and without various cross-linkers and under various freezing, conditions, are shown in FIGS. 3(a)–(k). Each of FIGS. 3(a)–(k) is a reproduction of an SEM micrograph, under each of which there is indicated the type of alginate used (see Table 1), its final percentage in the sponge solution (percentage w/v), the amount and type of cross-linker used, as well as the type of freezing used. i.e., where indicated by "freezer", a slow freezing process was used (−20° C., for 24 hours), or where not indicated, quick-freezing was used, i.e., freezing in liquid nitrogen (see FIGS. 3(a)–3(i)). As noted above, it was possible by the above equation to calculate the actual values of pore size and wall thickness from the SEM micrographs, and this by way of the bars printed on each micrograph, each bar representing 100 μm to provide an accurate means for measuring the values of pore size and wall thickness. These actual values are depicted graphically in FIGS. 4(a)–(d), which show the pore size (open bars) and the wall thickness (filled bars) from the various types of alginates with and without cross-linker and with or without "freezing" used in the preparation of the various sponges, as noted above.

Figure 3A:
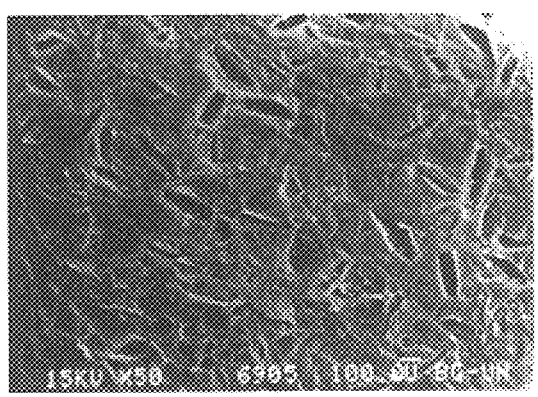
FIGS. 3(a)–(k) depicts reproductions of scanning electron microscopy (SEM) micrographs showing the morphology of various kinds of alginate sponges which may be made in accordance with the invention, as detailed in Example 2. LF 120 and HVCR are alginates as in Table 3, w/v is weight per volume, Ca-Gl is Calcium gluconate and $SrCl_2$ is Strontium chloride. The conditions used were the following (unless other specified, gels were frozen by liquid nitrogen)

Hence, the surface morphology by SEM of a representative sponge without cross-linking and with a rapid freeze-dry method is shown in FIG. 3(a) and the actual values of pore size and wall thickness of such a sponge is shown by the two lefthand bars (LFl) of FIG, 4(a). This sponge has also been shown to have the highest degree of shrinkage, probably due to the absence of the cross-linking network.

Figure 3B:
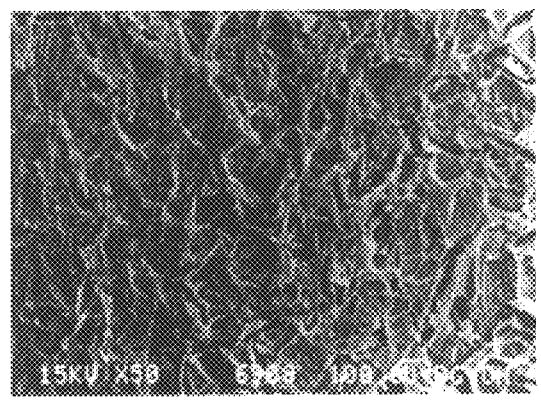

When, however, the sponges were prepared with a cross-linking agent, i.e., prepared from a cross-linked hydrogel, the sponge was highly porous, the degree of porosity and the pore size depending on the type and the concentration of the ionic cross-linker. Using calcium gluconate (Ca-Gl) as the cross-linker resulted in the formation of sponges with a homogenous microstructure both in terms of pore distribution and size, as illustrated in, FIGS. 3(b) and 3(c). The average pore size and wall thickness in this case were 100 and 50 μm, respectively, when using 0.1% (w/v) Ca-Gl, as shown in FIGS. 3(b) and 4(a) (see the middle bars of FIG. 4(a)) with a decrease in the average pore size and wall thickness as the concentration of Ca-Gl increased (see FIGS. 3(c) and 4(a) (the righthand bars)). Sponges prepared with calcium chloride or strontium chloride as the cross-linkers had, on the average, larger pores (compare FIGS. 3(c), 3(d) and 3(e), wherein the sponges in FIG. 3(c) were prepared with Ca-Gl, while the sponges of FIG. 3(d) were prepared with SrCl and those of FIG. 3(e) were prepared with CaCl). In the case where CaCl or SrCl were used as the cross-linkers, the average diameter of the pores was 150 and 200 μm, respectively, when similar concentrations (on a molar basis) of the ionic cross-linker were used, as shown in FIG. 4(b).

The viscosity of the alginate solution and the type of alginate, i.e., the comonomer ratio of guluronic (G) to mannuronic (M) acid residues, also had a significant effect on the sponge microstructure. Using the LF 20/60 polymer which has a similar G to M ratio as the LF 120, but which produces a less viscous solution, at 1% (w/v) polymer solution (see Table 1), resulted in the formation of a sponge with less homogenous microstructure (i.e., a less homogenous pore distribution, as shown when comparing FIGS. 3(f) to 3(c), which in both cases, the shown sponges were prepared in the same way with the same cross-linker (Ca-Gl) but differed by the type of alginate used, ie., LF 120 vs. LF 20/60). Further, the pore size was slightly smaller in the sponges prepared from the LF 20/60 alginate than those obtained from the LF 120 alginate sponges, and the wall thickness for the LF 20/60 alginate sponges was larger than that for the LF 120 alginate sponges, as shown in FIG. 4(b) (compare the lefthand bar to the righthand bar in this figure).

Figure 3C:
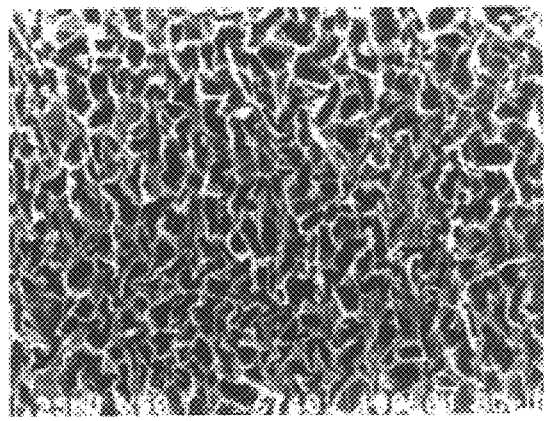
Figure 3D:
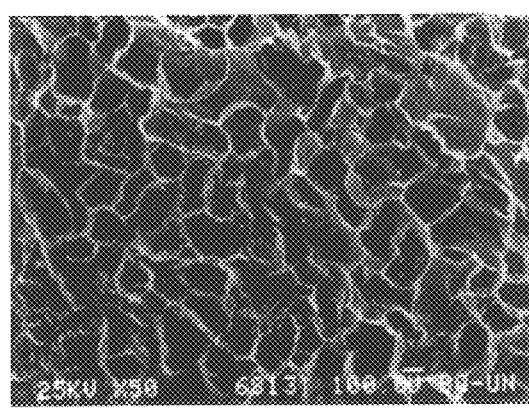
Figure 3E:
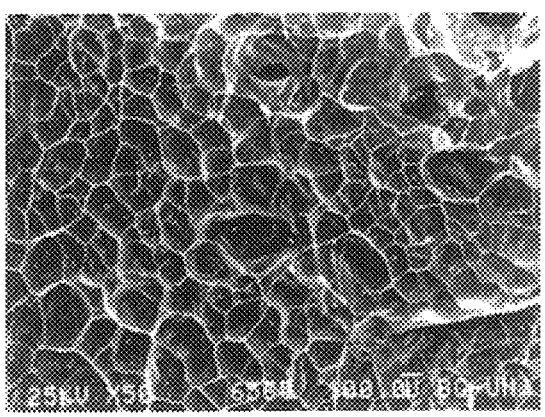
Figure 3F:
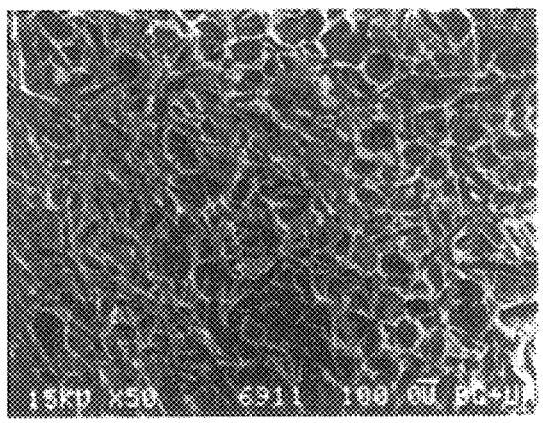
Figure 3G:
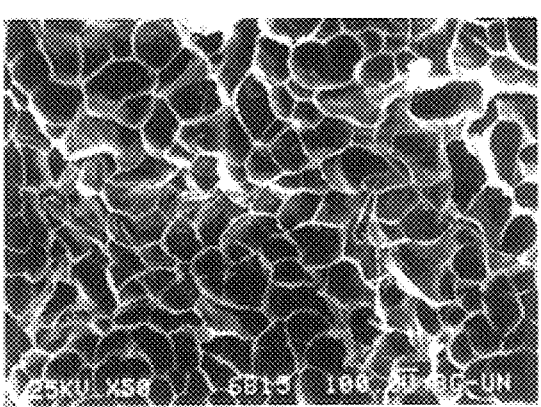
Figure 4A:
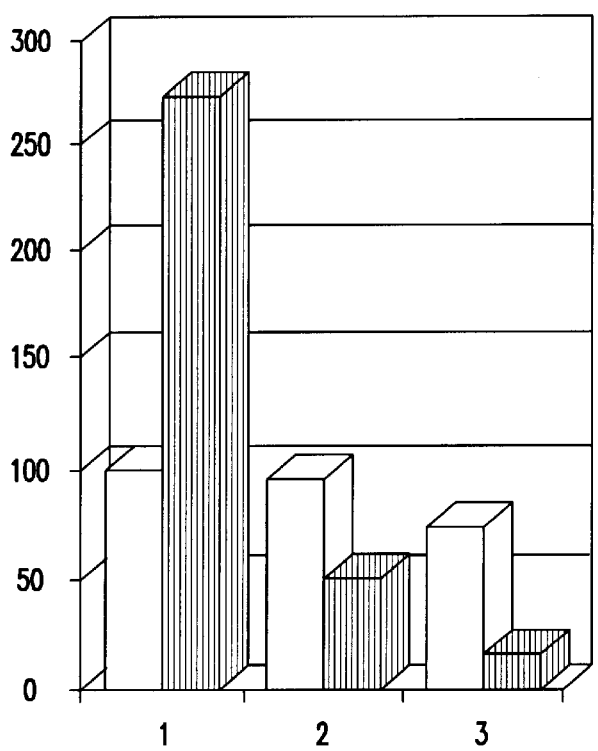
FIGS. 4(a)–(d) depict graphically by way of bar graphs the results showing the effects of changing various parameters of the process for production of the alginate sponges on the parameters of the microstructure of the resulting alginate sponges of the invention, as detailed in Example 2. White bars represent pore size measurements; shaded bars represent wall thickness measurements. Values on the ordinate are in micrometers [μ]. $CaCl_2$ is Calcium Chloride; Ca-Gl, Calcium Gluconate; $SrCl_2$, Strontium Chloride. Unless other specified, gels were frozen by liquid nitrogen.
Figure 4B:
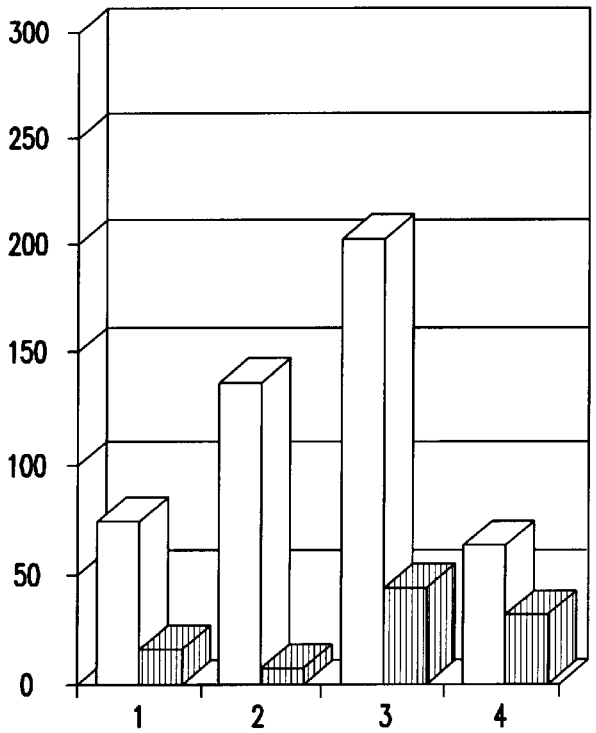
Figure 4C:
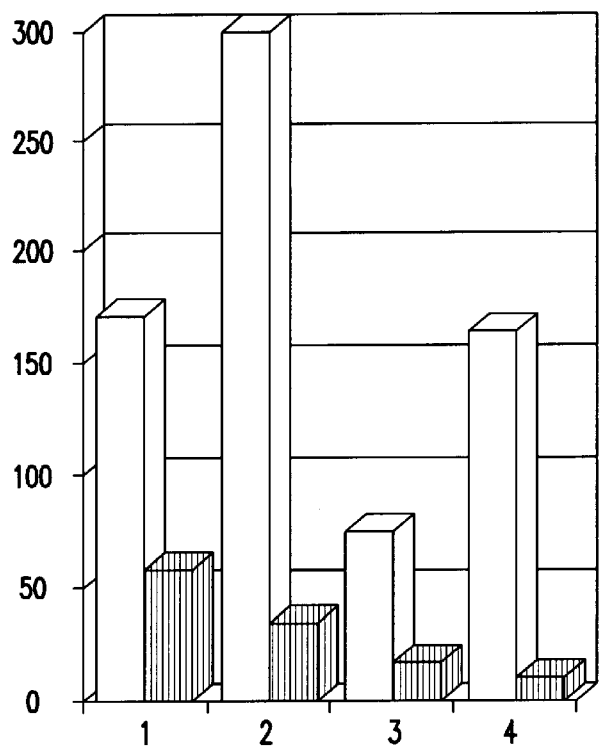
Figure 4D:
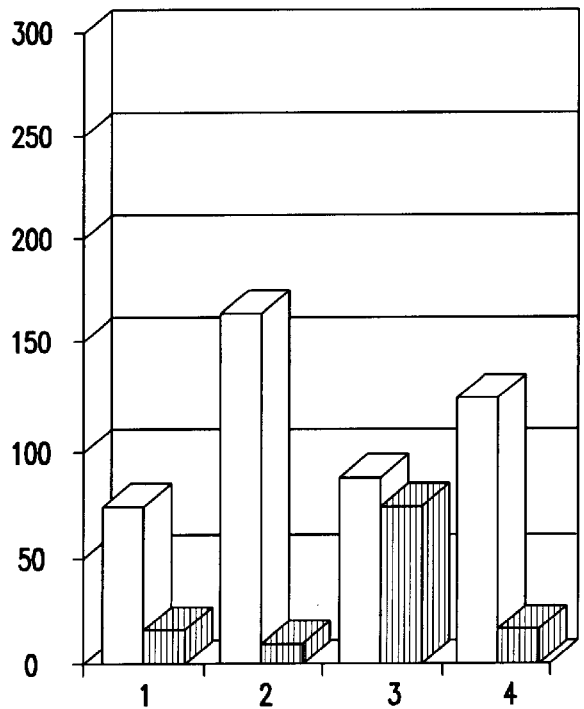

For a given alginate type, the initial alginate solution concentration significantly affected the sponge microstructure such that decreasing polymer concentration led to the production of sponges with an increasing pore size and decreasing wall thickness (see FIGS. 3(g) vs. 3(c) and FIG. 4(c), wherein the only difference between the sponges shown in FIG. 3(c) and those shown in FIG. 3(g) are in the amount of the alginate solution used, those of FIG. 3(g) prepared from an alginate solution but at half the concentration w/v of that used to prepare the sponges shown in FIG. 3(c).

Figure 3H:
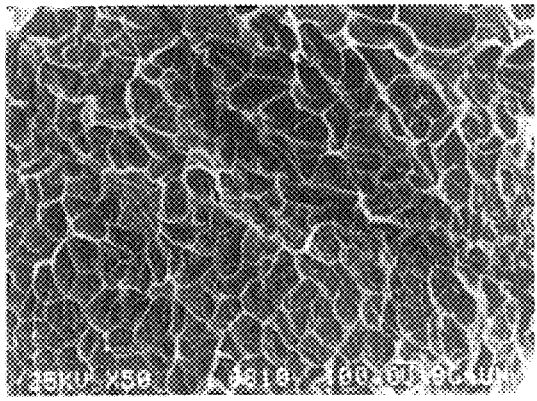
Figure 3I:
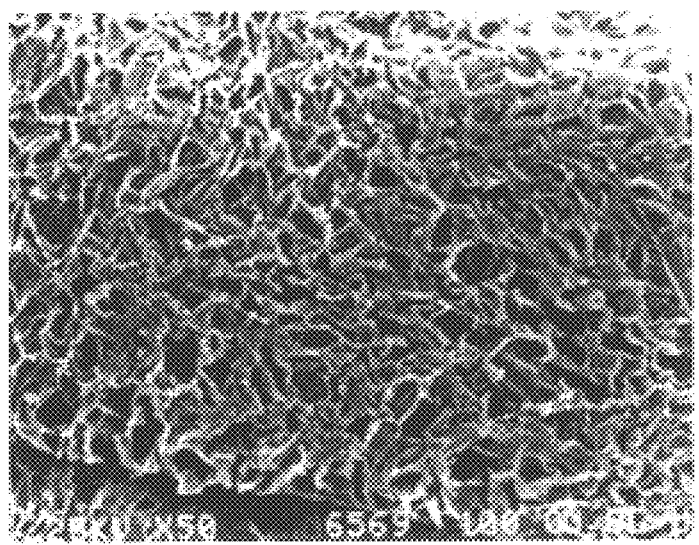
Figure 3J:
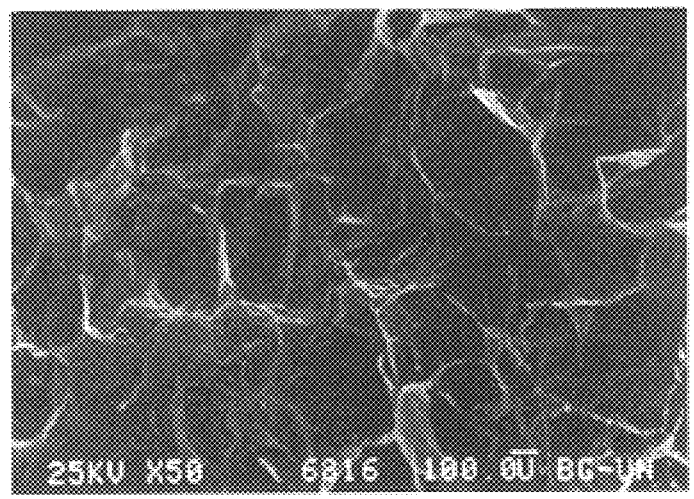
Figure 3K:
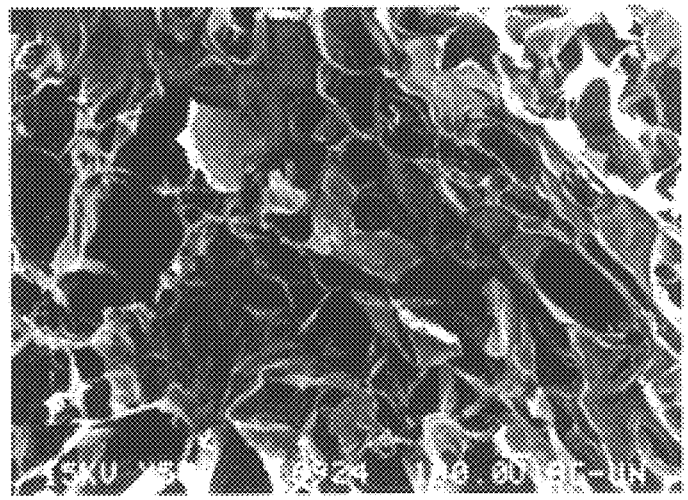

The alginate of the type HV-CR, which provided a solution of similar viscosity to that of LF 120, but had a lower guluronic content (see Table 1), led to the production of sponges with smaller pore sizes than those of the LF 120 alginate (see FIGS. 3(h) and 3(i), vs. FIGS. 3(g) and 3(c), wherein FIGS. 3(h) and 3(i) the sponges were prepared from HVCR alginate with the same cross-linker and same concentration of alginate solution and cross-linker solution as those prepared from the LF 120 alginate shown in FIGS. 3(g) and (c) respectively). The actual values of the pore sizes and wall thickness of the sponges produced with HVCR vs. those produced from LF 120 alginate are set forth in FIG. 4(d), i.e., compare the two sets of lefthand bars to the two sets of righthand bars in this figure. This result is in accordance with the theory of alginate gelation by ionic cross-linking, which correlates the gel-forming capabilities and gel pore size with the poly-G content of the polymer. According to the egg-box model of Grant et al. (1973), the bivalent cations bridge the negatively charged guluronic acid residues on the alginate, and the mannuronic residues play only a subordinate role in the gel framework. Thus, increasing the G content results generally with an increased pore size (see Martinsen et al., 1989).

The effect of the freezing process, i.e., the type and duration thereof on the sponge microstructure was also examined, and it was found that the quick freezing procedure, using liquid nitrogen, provided sponges with a smaller pore size and better mechanical properties (see below) than those obtained using the slow freezing process, i.e., freezing in a freezer at −20° C., for 24 hours. These differences are clearly illustrated in the comparison between FIGS. 3(c) and 3(g) with FIGS. 3(j) and 3(k), in which in the former, the liquid nitrogen freezing step was used, while in the latter the slow freezing process was used. The rest of the sponge constituents and preparative methods being the same in all cases, i.e., in all cases, the LF 120 alginate was used at two concentrations and as cross-linker, the Ca-Gl was used.

A comparison of actual values of the pore size and wall thickness obtained for the above sponges prepared by quick freezing or slow freezing are depicted in FIG. 4(c), wherein the two sets of lefthand bars represent sponges prepared by slow freezing, while the two sets of righthand-bars represent sponges prepared by quick-freezing. It is suggested that the differences between the pore sizes of the sponges prepared by the different freezing methods reflect the differences in the heat transfer rates during the freezing process. When the temperature is lowered, the water, still in liquid form, is supercooled to a temperature well below its freezing point. At this stage, ice crystals begin to form and heat of crystallization is released, which raises the temperature of the water up to its melting point, providing a mixture of ice and water. As a result, larger pores with thicker walls are produced during the slow freezing procedure. However, a sufficiently rapid rate of cooling, i.e., the quick freezing in liquid nitrogen, is considered to provide for the extraction of the heat of crystallization, which prevents the formation of large ice crystals. Further, following the freezing of the sponge material, the frozen material is dried under vacuum at a low temperature which provides the sublimation of ice crystals. Thus, the porosity of the sponges is controlled by the size of the crystals formed during the freezing process, namely, at a low freezing rate, e.g., freezing in a freezer at −18° C. to −20° C., for 24 hours, large ice crystals are formed, leading to the formation of a sponge with a crumbly microstructure and ruptured walls after the vacuum drying step, i.e., lyophilization. In contrast, a fast cooling step using liquid nitrogen results in the production of a large number of small ice crystals having a preferred orientation, thereby providing for the formation of a sponge with a homogenous microstructure and improved mechanical properties (see below).

The hereinabove described microstructure of the alginate sponges according to the present invention also differs significantly from that obtained by the known procedures for producing alginate hydrogels. In these known procedures (see Martinsen et al., 1989), the alginate hypogels are produced without freezing and lyophilizing and have a network of pores with pore size ranging between 50–1500 Å. The pore size of alginate hydrogel is probably controlled primarily by the density of the matrix cross-linking. This basic microstructure undergoes a substantial deformation caused by the freezing process during the production of the alginate sponge. During this freezing process, the growing ice crystals can break the cross-links leading to new microstructures. The frozen gel structure is thus a result of the formation and destruction of intrinsic bonds. Therefore, the composition of the gel (for example, the type of alginate and the presence or absence of cross-linkers and their relative concentrations) as well as the freezing rate used during the sponge preparation procedure have the greatest influence on the size and structure of the pores formed in the final sponge product, this being different from parameters which normally influence the microstructure of the previously produced alginate hydrogels, which are produced without subjection to freezing and/or lyophilization.

The above-mentioned results concerning the morphology of the sponges of the invention clearly indicate that the alginate sponge microstructure, in particular, the pore size and distribution, can be easily controlled and manipulated by varying the alginate composition and concentration, the type and concentration of the ionic cross-linker, and the freezing processing and rate of freezing. The ability, in accordance with the present invention, to produce a rather wide range of different types of alginate sponges with variable microstructures is highly important for the development of suitable implant substrates for cell transplantations and permits the optimization of such implants, for example, sponges of varying morphology, including microstructure, may be used for different types of implantations or transplantations, depending on the type of tissue into which the implants are to be placed, on the types of cells which it is desired to transplant.

The pore structure of an alginate sponge dictates the interaction of the sponge and transplanted cells contained therein with the host tissue into which such a sponge is inserted. The pore structure is determined by the size, size distribution, and continuity of the individual pores within the sponge. Porous materials are typically defined as microporous pore diameter<2 nm), mesoporous (2 nm<d<50 nm) or macroporous (d>50 nm). Only small molecules, for example, various gases, are capable of penetrating microporous materials. Mesoporous materials allow for the free transport of large molecules, and, when the pores are large enough (d>$10^4$ nm), then cells are capable of migrating through the pores of such a material. Thus, by careful design of a sponge, it is possible to produce a sponge which can allow desirable extracellular signals, for example, a rise in serum sugar concentrations, to be passed through the pores into the transplanted cells held within the sponge, while at the same time excluding larger extracellular molecular or cellular signals, for example, immunoglobulin molecules which act to cause rejection of the transplanted cells.

The sponges in accordance with the present invention belong to the macroporous materials, and hence they can allow for the vascularization of the matrix, which is very important for maintenance of cell viability and function of the transplanted cells held within the matrix (see, for example, Mikos et al., 1993). By way of the above process for manufacture of the sponges in accordance with the invention, it is possible also to produce alginate sponges which have a unimodal pore size distribution or a continuous pore structure. Such sponges allow molecules or cells to be transported though the sponge matrix without limitation ("bottlenecks") in the pore structure. Finally, as is apparent from the detailed description of the process for producing the sponges in accordance with the invention as set forth hereinabove, the present invention provides for a method for alginate sponge production that is simple to perform, is highly reproducible and is readily amenable to scaling up for commercial production of such sponges.

EXAMPLE 3

Mechanical Properties and the Pore Compressibility of the Alginate Sponges

The mechanical properties of alginate sponges were determined at 22° C. (room temperature) by compressing the sample sponges at a constant deformation rate of 2 mm/min, using a standard test apparatus. This apparatus is illustrated schematically in FIG. 5 and comprises a load cell, a deformation cell, and indentor, and a table. The sample sponge is placed between the indentor and the table and is subjected to a load which is measured by the measuring apparatus to which the table is connected at its other end ("translation"). With such an apparatus, the load and deformation were monitored with high accuracy down to loads of 1 g and at deformations of less than 0.05 mm. In this apparatus, the diameter of the indentor (7 mnm) was usually smaller than that of the sample (sample sponges being usually about 15 mm), or greater when subjected to compression, and hence the influence of sample diameter variations on the test results was minimized.

These tests of the mechanical properties and pore compressibility of the alginate sponges of the invention are highly important, in view of the fact that the sponges to be used for transplantations or implantations must have excellent mechanical properties and must maintain their shape during the stage of in vitro culturing including frequent medium replacements and finally, during the surgical procedure at the stage of transplantation. The results of the analysis of the mechanical properties, in particular, the compressibility of the various alginate sponges prepared in accordance with the invention, are depicted in FIGS. 6–11, which are graphical representations of the stress (kPa) versus the strain of the various sponges prepared using different tapes of alginate, different types of cross-linker, as well as varying concentrations of alginate and cross-linker, and different freezing conditions. FIGS. 6–11 thus represent a set of deformation curves on the stress-strain coordinate plane for the different types of alginate sponges prepared in accordance with the invention. Each curve depicted in FIGS. 6–11 represents the average result of 7–12 tests. In the tests, the variation coefficient was from 23 to 41% under minimal deformation and from 7 to 12% under maximal deformation conditions. The overall results from the curves shown in FIGS. 6–11 have also been summarized in Table 3.

alginate LF 120 solution with and without cross-linking, using different concentrations of calcium gluconate solution. Without cross-liking (the curve depicted with closed triangles) and with cross-linking but with a small amount of calcium gluconate (CaGl) of up to 0.1% by weight (dotted curve with closed squares), the sponges displayed the lowest rigidity, i.e., they deformed at relatively low loads. Upon increase in cross-linker concentration to 0.2% by weight (the solid curve with closed squares), a sharp increase in sponge rigidity was observed. In contrast, the guluronic acid (G) content of the alginate in the sponges did not have a significant effect on the mechanical properties of the sponge, as is apparent from the curves in FIG. 7. The modulus of elasticity of alginate sponges prepared from 1% (w/v) solutions of LF 120 (curve with closed triangles in FIG. 7) and HVCR (the solid curve with closed squares in FIG. 7) alginate, which have similar viscosity values (150 cP), but differ in their G content (LF 120 has 65–75% G, while HVCR has 39% G—see Table 1) are very similar, as is summarized also in Table 3. This behavior, it should be noted, is, however, different from that observed for the previously known alginate hydrogels, the mechanical properties of which highly depended on the content of G residues, with an increase in G content resulting in the formation of hydrogels that were stronger (see Smidsrod and Haug, 1972). Hence, the above results emphasize the structural as well as the behavioral differences between the sponges of the present invention and the previously known hydrogel format of alginates.

In FIG. 7 there is also shown that the solution viscosity greatly influenced sponge rigidity for a given alginate with a given G content. This is seen from the LF 20/60 alginate sponge (dotted curve with full squares in FIG. 7) which forms sponges having less rigidity than those formed from the LF 120 alginate solution (curve with full triangles in FIG. 7), the difference m the viscosity between LF 20/60 and LF 120 alginate being significant in that the LF 20/60 forms a less viscous solution of viscosity value of 100 cP vs. 150

TABLE 3

Mechanical properties and porosity of alginate sponges as a function of different formulation and processing parameters

| Alginate type | Alginate Conc. (%, w/v) | Cross-linker type | Cross-linker Conc. (%, w/v) | Regime of freezing | Average pore size ($\mu$m) | E-modulus elasticity (kPa) |
|---|---|---|---|---|---|---|
| LF120 | 1 | Ca-gluconate | 0.2 | liquid $N_2$ | 80 | 380 |
| LF120 | 0.5 | Ca-gluconate | 0.2 | liquid $N_2$ | 165 | 130 |
| LF120 | 1 | $CaCl_2$ | 0.1 | liquid $N_2$ | 135 | |
| LF120 | 1 | $SrCL_2$ | 0.15 | liquid $N_2$ | 200 | |
| LF120 | 1 | Ca-gluconate | 0.2 | freezer | 170 | 250 |
| LF 20/60 | 1 | Ca-gluconate | 0.2 | liquid $N_2$ | 60 | |
| HVCR | 1 | Ca-gluconate | 0.2 | liquid $N_1$ | 85 | 350 | liquid $N_2$-immediate freezing
freezer, -20° C., processing time

From the above-noted results depicted in FIGS. 6–11 and summarized in Table 3, it is apparent that the stress-strain behavior of alginate sponges was characteristic of the behavior of porous materials in which the modulus of elasticity increases with the strain. In FIG. 6. There is a comparison of the deformation curves of sponges prepared from 1% (w/v)

cP for LF 120. Hence, it is apparent that solution viscosity has a major influence on sponge rigidity.

Other parameters which greatly influenced the mechanical properties of alginate sponges prepared in accordance with the present invention include the type of cross-linker used. As shown in FIG. 8, sponges prepared with calcium chloride and strontium chloride had similar rigidity (see dotted curve with full squares and full curve with full squares, respectively, in FIG. 8), which rigidity was nevertheless significantly lower than that obtained when using calcium gluconate as the cross-linker (see curve with full triangle in FIG. 8). As noted above, as regards the morphology of the sponges, the sponges prepared using calcium gluconate as the cross linker had smaller pores, which may explain their enhanced The concentration of the alginate used in the preparation of the sponges also had a significant influence on the rigidity of the sponges. As depicted in FIG. 9, and as summarized in Table 3; an increase in the initial alginate concentration from 0.5 to 1% (w/v), for both low (HVCR) and high (LF 120) G content alginates resulted in sponges being produced having increased rigidity (compare the full curves with closed triangles and closed squares with the dotted curves with closed triangles and closed squares in FIG. 9, wherein the full curves denote the alginates at higher concentrations while the dotted curves for the alginates used at the lower concentrations). Thus, the higher the alginate concentration, the greater the required load to deform the sponges prepared therefrom. Further, as noted above as regards the morphology of the sponges made at different alginate concentrations, the results shown in FIG. 9 also indicate that the sponges having the highest rigidity were those having the smallest pore size.

Yet another parameter having marked influence on the rigidity of the sponges was that concerning the manner in which the sponges were produced and processed, in particular the freezing rate of the alginate solutions during the process of sponge preparation. In this respect, it was observed that fast freezing using liquid nitrogen yielded sponges having better mechanical properties, in particular, greater rigidity; with the result that sponges so-produced had to be subjected to higher loads to bring about deformation of the sponge. These results are depicted in FIG. 10. Which compares sponges prepared by fast freezing in liquid nitrogen to those prepared by slow freezing in a freezer, as noted above. Thus, for sponges prepared from LF 120 alginate at the higher concentration of 1% w/v and 0.2% by weight CaGl as cross-linker, it is clearly apparent that the sponges rapidly frozen in liquid nitrogen (solid curve with closed squares in FIG. 10) yielded sponges which were significantly more rigid than those prepared from the same alginate and cross-linker at the same concentrations thereof, but under conditions of slow freezing (dotted curve with closed squares in FIG. 10). In this analysis it is also interesting to note that for the sponges prepared from the lower concentration of the alginate, which were anyway shown to be less rigid than those prepared from higher concentrations of alginate (see FIG. 9), the effect of the different manner of freezing during the preparation thereof was not distinguishable, i.e., in both cases, sponges of greatly reduced rigidity were produced (see the two curves, one solid and one dotted, with closed triangles in FIG. 10).

If another parameter was studied for its effect on the rigidity of the sponges, this parameter being the effect of the sterilization of the sponges, which is required before using these sponges for cell culture and subsequent implantation and transplantation purposes, the results of this analysis indicated that sterilization of the sponges did not change their mechanical properties, as is depicted in FIG. 11. It is observed that sponges made from the higher concentration of LF 120 alginate and CaGl as crosslinker and subjected to rapid freezing in liquid nitrogen, did not have any significant change in their rigidity when subjected to gas-sterilization (compare the solid curve with closed squares depicting control sponges not gas-sterilized to the dotted curve with closed squares depicting the same sponges but which were subjected to gas sterilization, in FIG. 11). This finding, i.e., that gas sterilization of the sponges does not affect their mechanical properties in any observable manner, is of prime importance for the sponges of the present invention in view of their intended medical applications. Moreover, this finding further distinguishes the sponges of the present invention over sponges prepared from other materials, which other sponges have been known to be significantly affected when subjected to sterilization.

In summary, from the results set forth hereinabove concerning the morphology and mechanical properties of the various sponges produced in accordance with the present invention, it arises that the most preferred alginate sponges were those prepared from LF 120 at an initial alginate solution concentration of 1% w/v and cross-linked with calcium gluconate at 0.2% w/v and which underwent rapid freezing in liquid nitrogen followed by lyophilization during the process of the preparation. The various other sponges made with one or more variations of the above constituents and mode of preparation in accordance with the present invention are also perfectly useful for the intended purposes of these sponges, i.e., for cell culture and implantation or transplantation applications. Hence, in accordance with the present invention, it is possible to prepare a wide variety of sponges having different morphological and mechanical characteristics, all of which are useful, the most useful being the above-noted ones having the highest rigidity together with a more homogenous pore distribution.

EXAMPLE 4

Degradation of Alginate Sponges, in vitro

In order to determine the degradation of the alginate sponges of the present invention over a period of time, the sponges were incubated in a complete culture medium and samples were withdrawn at different time intervals for the purposes of assaying the concentration of soluble alginate by way of a calorimetric assay. This assay was based on the meta-chromatic change induced by alginate binding to the dye, 1,9-dimethyl methylene blue (DMMB) (see Halle et al., 1993).

In this assay, the alginate sponges were cultured in a standard culture medium being the standard complete medium usually used for culturing cells such as fibroblasts and hepatocytes, at 37° C. The cultured sponges were of two kinds, the one kind having been seeded with cells and the other being without any cells. Results of this assay show that alginate sponges, with or without seeded cells, cultured in culture medium at 37° C. maintained their physical stability for prolonged periods of time. Measurement of soluble alginate in the medium, being indicative of degradation of the alginate sponge, after a 1 month incubation period with or without cells, showed an insignificant concentration of soluble alginate in the culture medium (less than 1% w/v). A representative result of this analysis is depicted in FIG. 12, which is a reproduction of a light micrograph of sponges seeded with fibroblast cells and photographed and assayed after 1 month in culture medium at 37° C. In this case the sponge was prepared from LF 120 alginate, 1% w/v initial alginate solution and 0.2% w/v calcium gluconate as cross-linker, the preparation of which, as noted above, being inclusive of the step of rapid freezing in liquid nitrogen. From the above representative result shown in FIG. 12, it is apparent that the alginate sponges maintained their physical stability for the prolonged incubation time, further indicative of the usefulness of such sponges for prolonged cell culture and implantation and transplantation applications.

EXAMPLE 5

Hepatocyte Culture Within Alginate Sponges

Hepatocytes were isolated from 200–250 gr male Sprague Dawley rats using a modification of the three-step procedure of Berry and Fried (1969). The liver was perfused in the retrograde direction first with calcium-free perfusion buffer (143 mM NaCl, 150 mM KCl, 154 mM $NaHCO_3$, pH 7.4 and containing 9% w/v glucose for 5 mins followed by 100 mL of 5 mM EGTA, and finally with the same perfusion buffer but containing 5 mM $CaCl_2$ and 60 units/mL type IV collagenase, for 20 min. The disintigrating liver was dispersed in chemically defined serum-free culture medium (William's E with 10 ng/mL. EGF, 20 mU/mL insulin. 5 nM dexamethasone, 20 mM pyruvate, 2 mM L-glutamine, 100 U/mL penicillin/streptomycin, and 0.2 mM gentamycin). This medium is referred to herein as a "complete medium". Cell viability of the hepatocytes following dispersion was 80–90% as determined by the trypan blue exclusion assay. Dead cells and debris were removed by centrifurgation in an isodensity Percoll solution (see Kreamer et al., 1986), and the resulting cell pellet was then washed three times with a complete medium. Viability at plating of the so-prepared cells was 88–89%.

For routine culture, cells were plated in a complete medium, at a concentration of $3 \times 10^4$ viable cells/$cm^2$ culture surface area, or $6 \times 10^5$ cells-dish, for the 50-mm control dishes. The control dishes were treated with collagen type I (collagen coverage at a concentration of 1 $\mu g/cm^2$), to support hepatocyte growth.

For cell culture within alginate sponges, sponges of the invention with the following dimensions were used: $15 \times 10$ mm (diameter×height) and volume of 1.7 $cm^3$, made from LF 120 (the initial concentration of alginate solution and calcium gluconate were 1 and 0.2% w/v, respectively). The sponge was placed in a well of 24-well polystyrene plates. Hepatocytes were seeded at a concentration of $1 \times 10^6$ cells/mL as follows: $2 \times 10^5$ cells suspended in 200 $\mu$L complete medium were overlayered on top of the dry sponges. Due to their hydrophilic nature, the sponges were wetted instantly by the medium (air within the pores was replaced by the liquid), thus pulling the cells by capillary forces into the sponge pores. This resulted in a more homogenous distribution of the cells within the sponge The seeded sponges were incubated without any additional medium, in a 5% $CO_2$ incubator, at 37° C., with 99% humidity, for 1 hr. then 1-mL of the complete medium was added. Following an attachment period of 3–5 h (maximum attachment to all alginate gels occurred within 3 h), the medium was changed to remove unattached cells, and then the cells were maintained in complete medium with daily medium changes.

At different times of cell culture, the number of cells in the control (collagen-coated) and experimental (alginate sponges) dishes was measured by direct counting or by biochemical assays as detailed below. after the cell layer or sponge had been washed twice with PBS. For each measurement, triplicate dishes or sponges were used.

The following direct counting and biochemical assays were performed:

(a) Direct counting: For direct counting, cells were removed from the control dishes using 0.05% trypsin/EDTA; from alginate sponges cells were released after dissolving the sponges with 1 mL citrate buffer 4% (w/v), pH 7.4. The number of cells was determined by direct counting on a hemacytometer.

(b) By LDH test: Lactate dehydrogenase (LDH) activity was determined using Sigma Kit (LDH/LD No. DG1340-UV). Cell number was determined by measuring the enzyme activity after cell lysis by 3 cycles of freeze-thaw (−20° C.–37° C.). A standard calibration curve was constructed using different dilutions of the stock cell culture. A linear relationship between the LDH activity and cell number was observed up to cell concentration of $3 \times 10^6$ cell/ml.

(c) By MTT: The MITT assay is based on the ability of mitochondrial dehydrogenase enzymes of living cells to convert the soluble yellow MTT salt (3(4,5-dimethyl-thiazol-2-yl)-2,5 diphenyl-tetrazolium bromide) into the insoluble purple formazan salt. MTT (Sigma) was prepared as a 5 mg/ml stock solution in PBS (phosphate buffered-saline). The undissolved residues were removed by sterile filtration. The stock solution was stored in the dark at 4° C. and used within 3 wk of preparation. MTT stock solution of 60 $\mu$l was added into the well of a 24-well polystyrene plate, containing the sponge in 1 mL culture medium. Following an incubation period of 5 h, at 37° C., the MTT conversion was stopped upon removal, by vacuum aspiration, of the MTT containing medium from the wells. The resultant insoluble formazan product was dissolved in 100 ml of isopropanol-0.04 N HCl solution (250:1, volume ratio), and the absorbance of the solution was measured at 560 nm against a blank of isopropanol-HCl.

(d) By DNA: Total DNA content was determined according to the method of Brunk et al. (1979). This method can detect the DNA concentration of a crude cellular homogenate accurately, in the nanogram range, using the fluorescence enhancement of 4',6-diamidino-2-phenyllindole (DAPI) completed with DNA. Briefly, cell-seeded sponges were treated with citrate buffer to dissolve the sponges and release the cells. The cells were lysed by performing 2 cycles of freeze-thaw (−20° C.–37° C.), followed by their dispersion in 25 mL of 1 M NaOH, and boiling the mixture for 30 min. After neutralization with HCl, and cooling to room temperature, the fluorescent dyre, DAPI, at 100 ng/100 mL Tris buffer, pH 7.0, was added. The fluorescence emission of the samples at 540 nm was determined upon sample excitation at 286 nm. The number of cells was estimated from a calibration curve using known concentration of cells.

(e)Determination of albumin secretion

Albumin secretion into the culture medium was quantified by a sandwich enzyme-linked immunosorbent assay (Schwerer et al., 1987) using antibodies specific for rat albumin. Briefly, 96-well polystyrene plates (Nunc Immuno plate) were coated with 100 $\mu$L of sheep anti-(rat albumin), 2 $\mu$g/mL, in coating carbonate buffer, pH 9.0, overnight, at 4° C. After washing the plates with PBS container 0.05% v/v Tween 20 (PBS-Tween), they were blocked by adding 100 $\mu$L of 1% (w/v) gelatin to reduce non-specific binding. After incubating for 1 hr at room temperature, the plates were washed three times with PBS-Tween, and 100 $\mu$L of the appropriate diluted samples of the medium w as added to the wells. After 2 h incubation at room temperature, the wells were washed as described above, followed by the addition of 100 $\mu$L peroxidase-conjugated rabbit anti-(rat albumin) in PBS (1:4000 dilution from stock), at room temperature. After 2 h incubation, the wells were washed with PBS-Tween, and 100 $\mu$L of the substrate 2,2'-Azino-di-(3-ethylbenzthiazoline sulphonaze) (ABTS) (1 mg/mL, in 77 mM Na phosphate/61 mM citrate buffer, pH 4.0 containing 0.01% (v/v) $H_2O_2$) was added into each well and incubated for 1 h, at 37° C. The enzymatic reaction was stopped by the addition of 0.32% (w/v) sodium fluoride, and the color change was monitored spectrophotometrically at 405 nm against a reference at 490 nm using the ELISA Reader (Denlev, WS050 WellScan). Pure rat albumin (Cappel) was used for establishing a standard curve.

The results of the above analysis of the hepatocytes cultured within the alginate sponges are as follows:

Initially, the cultured hepatocytes were observed under light microscopy to asses the overall morphology and nature of the cells cultured in the alginate sponges. A representative reproduction of a light micrographs taken at different durations of incubation is shown in FIG. 13, in which the upper micrograph shows cells at the time of seeding (day 1 of incubation), and the lower micrograph shows cells after 10 days in culture, the magnification in both micrographs being the same.

From the light micrographs shown in FIG. 13, there are observed several unique features, compared with conventional culture on collagen-treated dishes: 1) the hepatocytes are immobilized mainly within the pore of the alginate sponge; (2) the morphology of the hepatocytes is spherical throughout the culture, rather than the flat, extended shape as usually found in monolayer culture, this spherical morphology being close to that observed in vivo; and (3) at some parts of the sponge spheroids of hepatocytes can be observed (see in particular the upper micrograph in FIG. 13). Further, it is clearly apparent from both micrographs in FIG. 13 that in the 10 days of culture (compare top to bottom micrographs), a great amount of cell proliferation occurred.

To analyze the number of hepatocytes within the alginate sponge, hepatocytes were released from the matrix by dissolving it with citrate buffer. The number of cells at different incubation times was assayed by LDH and DNA contents as noted above. The results are presented in FIG. 14. a graphical representation of the number of cells as a function of time (days in incubation). These results show that cells proliferated within the sponges (as seen primarily by the increase in DNA synthesis). This pattern of differentiated function by cells undergoing DNA synthesis within the alginate sponges is similar to the reported behavior of hepatocytes in regenerating liver (see Friedman, 1984).

To examine how hepatocytes function within the alginate sponges, the capability of these cells to secrete albumin was examined. The results presented in FIG. 15, a graphical representation of the amount of albumin secreted ($\mu$g/day/ $10^6$ cells) by the cells as a function of time (days in incubation). These results show that the secretion of albumin from hepatocytes grown within the alginate sponges was stable over 10 days of culture (see the results indicated with filled triangles in FIG. 15). In contrast, in the conventional culture (collagen-treated dishes), the secretion of albumin declined with the culture time and was almost lost after 5 days of culture.

EXAMPLE 6

Fibroblast Culture Within Sponges

Sponges with an average size of 15×10 mm (diameter× height), and approximate volume of 1.7 $cm^3$, in a well of 24-well polystyrene plates, were seeded with 2×$10^5$ normal dermal fibroblasts obtained from human foreskin, suspended in (200 $\mu$L) of DMEN medium supplemented with 10% fetal calf serum (DMEM-FCS). The seeded sponges were incubated without any additional medium, in a 5% $CO_2$ incubator, at 37° C., with 99% humidity for 1 hr, then 1-mL of DMEM-FCS were added. The medium was replaced every three days.

Fibroblasts seeded within the alginate sponges were then analyzed by scanning electron microscopy (SEM). For this purpose, samples were taken from the seeded sponges in incubation and fixed for scanning electron microscopy (SEM). Briefly, the sponges were washed with PBS and then fixed in PBS buffer containing 2% glutaraldehyde (pH 7.4) for 1 hr at room temperature, followed by 24 hr at 4° C. After washing with PBS buffer twice, the sponges were dehydrated through a graded series of ethanol soaks (10–99.8% in 10% increments) for 10 min each. The samples were critical-point dried and coated with an ultrathin gold layer (100 Å) as described above.

Usually, the above assay by SEM was carried out after 5 days of culture of the fibroblast-seeded alginate sponges.

As in the case of the hepatocytes (see above), the fibroblasts preferred the pores of the alginate sponge (FIG. 16). This is readily observable in the SEM micrographs shown in FIG. 16, which are but representatives of a large number of similar micrographs prepared from a number of such fibroblast-seeded sponge samples. The micrographs in FIG. 16 show two magnification levels: a high one (upper micrograph) and a lower one (lower micrograph), from which it is apparent that the fibroblasts grow within the pores of the sponge. It should be noted in FIG. 16 that both micrographs also include a printed bar which provides a scale for determining the actual sizes of the cells, pores, pore wall thickness, etc. The bar in the upper micrograph represents 10 $\mu$m and the bar in the lower micrograph represents 100 $\mu$m. Further, the adhesion of the cells and their proliferation with culture time had no significant effect on the sponges, which maintained their original shapes (results not shown). This demonstrates yet another advantage of the alginate sponge material over collagen sponges. Previous studies have shown that fibroblasts grown on collagen contract the newly synthesized collagen layer on which they are growing, resulting in a "roll-up" of the cell monolayer (see Rivard et al., 1995). In a similar fashion, the seeded collagen foams were also contracted, down to approximately 40% of their initial volume, after 5 weeks of culture (Rivard et al., 1995), which made them inappropriate for the transplantation of a large mass of cells.

EXAMPLE 7

Encapsulation of Protein-containing MicrosPheres Within Alginate Sponges

To enhance the vascularization of sponges intended for cell growth in vivo, angiogenesis factors can be inserted into the sponges. However, alginate or other polysaccharide sponges are too porous for the effective encapsulation of proteins or peptides, and these molecules rapidly escape from the matrix. To prolong their delivery from the sponge, these factors can be first encapsulated within tiny, biodegradable, controlled-release microspheres, such as poly(lactic/glycolic acid), which will then be entrapped within the sponge.

Thus, poly(lactic/glycolic acid) microspheres, containing fibroblast growth factors, or any other angiogenesis factor, were prepared by the solvent evaporation method based on a double emulsion (Cohen et al., 1991). The resultant microspheres, having a diameter in the range of 5–20 $\mu$m, were added to the alginate solution immediately after adding the cross-linking solution, while stirring intensively using the process of the invention (for details, see Example 1). The alginate gels were then frozen and lyphilized as in Example 1, to yield a sponge containing microspheres which themselves contained the above factors.

FIG. 17 is a reproduction of a SEM of the resultant sponge. The upper micrograph is a lower magnification and the lower micrograph is a higher magnification, showing that the microspheres are within the pores of the sponge. The bars in both micrographs represent the scale for determining the actual size parameters of the pore size and pore wall thickness of the sponge, and the size of the microspheres within the sponge.

REFERENCES

[1] I. V. Yannas, Biologically active analogues of the extracellular matrix: artificial skon and nerves, Asres. Chera. Int. Ed. Enr. 29 (1990) 20–35.
[2] T. Natsume, O. Ike, T. Okada, N. Takimoto, Y. Shimizu and Y. Ikada, Porous collagen sponge for esophageal replacement. J. Bionaed. Mater. Res. 27 (1993) 867–875.
[3] D. A. Grande, M. I. Pitman, L. Peterson, D. Menche and M. Klein, The repair of experimentally produced defects in rabbit articular cartilage by autologous chondrocyte transplantation, J. Orthop. Res. 7 (1989) 208–218.
[4] C. A. Vacanti, R. Langer, B. Schloo and J. P. Vacanti, Synthetic Biodegradable Polymers Seeded with Chondrocytes Provide a Template for New Cartilage Formation In Vivo., J. Pediat Surgery (In Press) (1990)
[5] A. G. Mikos, G. Sarakinos, M. D. Lyman, D. E. Ingber, J. P. Vacanti and R. Langer, Prevascularization of porous biodegradable polymers, Biotech. Bioeng, 42 (1993a) 716–723.
[6] A. G. Mikos, Y. Bao, L. G. Cima, D. E. Ingber, J. P. Vacanti and R. Langer, Preparation of poly(glycolic acid) bonded fiber structures for cell attachement and transplantation, J. Biomed. Mater. Res. 27 (1993b) 11–23.
[7] A. G. Mikos, G. Sarakinos, S. M. Leite, J. P. Vacanti and R. Langer, Laminated three-dimensional biodegradable foams for use in tissue engineering, Biomaterials 14 (1993c) 323–330.
[8] R. Langer and J. P. Vacanti, Tissue engineering, Science 260 (1993) 920–926.
[9] K. Jain, R. A. Berg and G. P. Tandon, Mechanical stress and cellular metabolism in living soft tissue composites, Biomaterials 11 (1990) 465–472.
[10] K. J. Doane and D. E. Birk, Fibroblasts retain their tissue pheontype when grown in three-dimensional collagen gels. Exp. Cell. Res. 195 (1991) 432–442.
[11] J. Folkman and A. Moscona, Role of cell shape in grown control, Nature 273 (1978) 345–349.
[12] J. A. Madri and M. D. Basson, Extracellular matrix-cell interactions:dynamic modulators of cell, tissue and organism structure and function, Lab. Invest. 66 (1992) 519–521.
[13] L. H. H. Olde Damink, P. J. Dijkstra, M. J. A. Van Luyn, P. B. Van Wachem, P. Nieuwenhuis and J. Feijen, Changes in the mechanical properties of dermal sheep collagen during in vitro degradation, J. Biomed. Mater Res. 29 (1995) 139–147.
[14] A. Ben-Yishay, D. A. Grande, R. E. Schwartz, D. Menche and M. D. Pitman, Repair of articular cartilage defects with collagen-chondrocytes allografts, Tissue Engineering 1 (1995) 119–132.
[15] R. Timple, K. Mark and H. Mark, Immunochemistry and Immunohistology of collagens, in: A. Viidik and J. Vuust (Eds.), Biology of Collagen, Academic Press, 1980, pp. 211.
[16] T. G. Park Lu, T. and Crotts. G., Importance of in-vitro experimental conditions on protein release kinetics, stability and polymer degradation in protein encapsulated poly(D,L-lactic acid-co-glycolic acid) microspheres., journal of controlled release 33 (1995) 211–222.
[17] L. Sennerby, T. Rostlund, B. Albrektsson and T. Albrektsson, Acute tissue reactions to potassium alginate with and without colour/flavor additives, Biomaterials 8 (1987) 49–52.
[18] S. Cohen, H. Bernstein. C. Hewes, M. Chow and R. Langer, The pharmacokinetics of and humoral responses to antigen delivered by microencapsulated lidosomes, Proc. Natl. Acad. Sci. USA (In Press) (1991)
[19] G. A. Kin, A. J. Daugulis, P. Faulkner and M. F. A. Goosen, Alginate-Polylysine Microcapsules of Controlled Membrane Molecular Weight Cutoff for Mammalian Cell Culture Engineering, Biotechnology Progress 3 (1987) 231–240.
[20] A. M. F. Sun. M. F. A. Gocsen and G. O' Shea, Microencapsulated Cells as Hormone Delivery Systems, CRC Crit. Rev. Drug Carriers Sys. 4 (1987) 1–12.
[21] J. P. Halle, D. Landry, A. Fournier, M. Beaudry and A. Leblond, Method for the quantification of alginate in microcapsules, Cell Transplantation 2 (1993) 429–436.
[22] M. N. Berry and D. S. Friend, High yield preparation of isolated rat parenchymal cells. A biochemical and fine structure study, J. Cell. Biol. 43 (1969) 506–520.
[23] B. L. Kieamer, J. L. Stuecker and e. al., Use of low speed, 150-density Percoll centrifugation method to increase the viability of isolated rat hepatocyte preparations, In Vitro Cell Dev. Biology 22 (1986) 201–207.
[24] C. F. Brunk, K. C. Jones and T. W. James, Assay for nanogram quantities of DNA in cellular homogenates, Analitical Biochem, 92 (1979) 497–500.
[25] B. Schwerer, M. Bach and H. Bernheimer, ELISA for determination of albumin in the nanogram range: assay in cerebrospinal fluid and comparison with radial immunodiffusion. Clinical Chim. Acta 163 (1987) 237–244.
[26] B. F. Matlaga, L. P. Yasenchak and T. N. Salthouse, Tissue response to implanted polymers: the significance of sample shape, J. Biomed. Mater. Res. 10 (1976) 391–397.
[27] G. T. Grant, E. R. Morris, D. A. Rees. P. J. C. Smith and D. Thom, Biological interactions between polysaccharides and divalent ctions: The egg box model., FEBS Lett. 32 (1973) 195–8.
[28] A. Martinsen, G. Skjak-Braek and O. Smidsrod, Alginate as immobilization material: I. correlation between chemical and physical properties of alginate gel beads, Biotechnol. Bioeng. 33 (1989) 79–89.
[29] O. Smidsrod and A. Haug. Properties of poly(1,4-hexuronates) in the gel state. II Comparison of gels of different chemical composition, Acta Chem. Scand. 26 (1972) 79–88.
[30] J. W. Friedmnan. E. Y. Chang and J. Darnell J. E., J. Mol. Biol. 179 (1984) 37–53.
[31] C. H. Rivard, C. J. Chaput, E. A. DesRosiers, L. H. Yahia and A. Selmani, Fibroblasts seeding and culture in biodegradable porous substrates, J. Appl. Biomater. 6 (1995) 65–68.
[32] S. Cohen, T. Yoshioka, M. Lucarelli, L. H. Hwang and R. Langer, (1991) Pharm. Res. 8, 713–720.

What is claimed is:

1. A process for producing a polysaccharide sponge characterized by having: (i) an average pore size in the range between about 10 μm to about 300 μm; (ii) an average distance between the pores being the wall thickness of the pores in the range between about 5 $\mu$m to about 270 $\mu$m; and (iii) an E-modului of elasticity being a measure of the rigidity of the sponge in the range of about 50 kPa to about 500 kPa, the process comprising:

(a) providing a polysaccharide solution containing about 1% to about 3% w/v polysaccharide in water;

(b) optionally diluting said polysaccharide solution with additional water to obtain a final solution having about 0.5% to about 2% w/v polysaccharide, and subjecting said solution of (a) to gelation, to obtain a polysaccharide gel;

(c) freezing the gel of (b); and (d) drying the frozen gel of (c) to obtain a polysaccharide sponge.

2. A process according to claim 1, further comprising the addition of a cross-linker to said polysaccharide solution of (a) during the step of gelation (b), said cross-linker being added in an amount to provide a concentration of cross-linker in the final solution being subjected to gelation of between about 0.1% to about 0.3% w/v.

3. A process according to claim 1, wherein said polysaccharide solution of (a) is prepared by dissolving the polysaccharide in powdered form in double distilled water in amounts to yield a concentration between about 1% to about 3% w/v polysaccharide in said solution, said polysaccharide solution being mixed in a homogenizer at about 25000 RPM for about 30 minutes at room temperature.

4. A process according to claim 1, wherein the gelation step (b) is by intensive stirring of the polysaccharide solution in a homogenizer at about 31800 RPM for about 3 minutes, and wherein when a cross-linker is added to the solution, said cross-linker is added very slowly during said intensive stirring of the polysaccharide solution.

5. A process according to claim 1, wherein said polysaccharide comprises an alginate derived from brown sea algae selected from the group consisting of alginate Protanal™ LF 120 (LF 120) derived from *Laminaria hyperhorea*, alginate Protanal™ LF 20/60 (LF 20/60) derived from *Laminaria hyperborea*, alginate MVG™ (MVG) derived from *Laminaria hyperborea*, alginate Pronatal™ HF 120 (HF 120) derived from *Laminaria hyperborea*, alginate Pronatal™ SF 120 (SF 120) derived from *Laminaria hyperborea*, alginate Pronatal™ SF 120 RB (SF 120 RB) derived from *Laminaria hyperborea*, alginate Pronatal™ LF 200 RB (LF 200 RB) derived from *Laminaria hyperborea*, alginate Manugel™ DMB (DMB) derived from *Laminaria hyperhorea*, Keltone™ HVCR (HVCR) derived from *Macrocystis pyrifera*, and Keltone™ LV (LV) derived from *Macrocystis pyrifera*.

6. A process according to claim 5, wherein in said process, the final solutions subjected to gelation in step (b) are selected from the group consisting of: (i) LF 120 alginate 1% w/v without cross-linker; (ii) LF 120 alginate 1% w/v and Ca-Gl 0.1% w/v; (iii) LF 120 alginate 1% w/v and Ca-Gl 0.2% w/v: (iv) LF 120 alginate 1% w/v and $SrCl_2$ 0.15% w/v; (v) LF 120 alginate 1% w/v and $CaCl_2$ 0.1% w/v; (vi) LF 120 alginate 0.5% w/v and Ca-Gl 0.2% w/v; (vii) LF 20/60 alginate 1% w/v and Ca-Gl 0.2% w/v; (viii) HVCR alginate 0.5% w/v and Ca-Gl 0.2% w/v; and (ix) HVCR alginate 1% w/v and Ca-Gl 0.2% w/v.

7. A process according to claim 1 wherein said freezing step (c) is by rapid freezing in a liquid nitrogen bath at about −80° C. for about 15 minutes.

8. A process according to claim 1 wherein said freezing step (c) is by slow freezing in a freezer at about −18° C. for about 8–24 hours.

9. A process according to claim 1 wherein said drying step (d) is by lyophilization under conditions of about 0.007 mmHg pressure and at about −60° C.

10. A process according to claim 4 wherein the final polysaccharide solution with or without cross-linker is poured into a vessel of desired shape before commencement of the intensive stirring of the gelation step (b), said vessel having a shape that is desired for the shape of the polysaccharide sponge.

* * * * *